(12) United States Patent
Patron et al.

(10) Patent No.: US 6,433,134 B1
(45) Date of Patent: Aug. 13, 2002

(54) PEPTIDE NUCLEIC ACID PRECURSORS AND METHODS OF PREPARING SAME

(75) Inventors: Andrew P. Patron, San Diego; Azra Pervin, San Marcos, both of CA (US)

(73) Assignee: Biocept, Inc., Carlsbad, CA (US)

( * ) Notice: Subject to any disclaimer, the term of this patent is extended or adjusted under 35 U.S.C. 154(b) by 0 days.

(21) Appl. No.: 09/479,320

(22) Filed: Jan. 5, 2000

Related U.S. Application Data

(63) Continuation-in-part of application No. 09/113,211, filed on Jul. 9, 1998.

(51) Int. Cl.$^7$ .................. C07K 7/00; C07H 21/00; C07H 19/04; C07D 473/00; C07D 401/00
(52) U.S. Cl. .............. 530/300; 530/333; 536/22.1; 536/26.7; 536/26.8; 536/25.3; 544/264; 544/265; 544/296; 544/310
(58) Field of Search .................. 530/333, 300; 536/22.1, 26.7, 26.8, 25.3; 544/264, 265, 310, 296

(56) References Cited

U.S. PATENT DOCUMENTS

| | | | |
|---|---|---|---|
| 5,539,082 A | | 7/1996 | Nielsen et al. ............ 530/300 |
| 5,539,083 A | * | 7/1996 | Cook et al. ............... 530/333 |
| 5,641,625 A | | 6/1997 | Ecker et al. ................. 435/6 |
| 5,681,947 A | | 10/1997 | Bergstrom et al. .......... 536/286 |
| 5,714,331 A | | 2/1998 | Burchardt et al. ............ 435/6 |
| 5,736,336 A | | 4/1998 | Burchardt et al. ............ 435/6 |
| 5,738,996 A | | 4/1998 | Hodges et al. ............. 435/7.1 |
| 5,766,855 A | | 6/1998 | Burchardt et al. ............ 435/6 |
| 5,773,571 A | | 6/1998 | Nielsen et al. ............ 530/300 |
| 5,817,811 A | | 10/1998 | Breipohl et al. ........... 544/264 |
| 5,936,077 A | | 8/1999 | Pfleiderer et al. .......... 536/23.1 |

FOREIGN PATENT DOCUMENTS

| | | |
|---|---|---|
| WO | 8605518 | 9/1986 |
| WO | 8605519 | 9/1986 |
| WO | 9220702 | 11/1992 |
| WO | 9220703 | 11/1992 |
| WO | 9514706 | 6/1995 |
| WO | 9523163 | 8/1995 |
| WO | 9611205 | 4/1996 |
| WO | 9615143 | 5/1996 |
| WO | 9620212 | 7/1996 |

* cited by examiner

*Primary Examiner*—Mukund J. Shah
*Assistant Examiner*—Tamthom N. Truong
(74) *Attorney, Agent, or Firm*—Fitch, Even, Tabin & Flannery

(57) ABSTRACT

Novel and efficient syntheses create novel piperazinone intermediates which facilitate the production and use of PNAs. Such syntheses and the products enhance the feasibility of a system which permits the rapid identification of PNA oligomers useful as therapeutics, diagnostics and/or gene characterization tools. A first component of the system is a universal PNA library that most preferably incorporates one or more universal nucleotide bases into carefully selected positions within each oligomer species thereby providing the library with the screening ability of a much larger library. The second component of the system is a high throughput screening system that includes a number of assays designed to provide information on the binding activities of the different PNAs to a target nucleotide sequence (generally, a DNA or RNA sequence). The third component is a software system especially designed to provide rapid analysis of the data collected from the high throughput screening system and to determine therefrom the sequence base identities and sequence lengths of PNA oligomers most likely to bind to and appropriately affect the target molecule.

18 Claims, 12 Drawing Sheets

PEPTIDE NUCLEIC ACID PRECURSORS AND METHODS OF PREPARING SAME

This application is a continuation-in-part of U.S. Ser. No. 09/113,211, filed Jul. 9, 1998, the disclosure of which is incorporated herein by reference.

The invention relates to methods of synthesizing peptide nucleic acids and to libraries that are prepared with such peptide nucleic acids. More particularly, it relates to economical methods for preparing activated and protected cyclic intermediates that provide peptide nucleic acid monomers, to libraries containing oligomers that can be synthesized using such monomers, and to systems for using such libraries in research and/or diagnosis.

BACKGROUND OF THE INVENTION

Reagents that selectively bind to DNA or RNA are of significant interest in molecular biology and medicinal chemistry as they may be developed into gene-targeted drugs for diagnostic and therapeutic applications and may be used as tools for sequence-specific modification of DNA. To date, research directed at identifying such reagents has focused primarily upon development of various oligonucleotides and their close analogs having modified backbones, such as, phosphorothioate or methyl phosphonate backbones instead of the natural phosphodiester backbone. These reagents, however, have been found to have serious shortcomings, especially with respect to stability against biological degradation, solubility, cellular uptake properties and ease of synthesis. For these reasons, alternative concepts for oligonucleotide mimics have been attracting interest.

Peptide nucleic acids (PNAs) are a recently developed class of oligonucleotide mimics wherein the entire deoxyribose phosphate backbone has been replaced by a chemically different, structurally homomorphous backbone composed of (2-aminoethyl)glycine units. Despite this dramatic change in chemical makeup, PNAs recognize complementary DNA and RNA by Watson-Crick base pairing. Furthermore, PNAs have been shown to have numerous advantages over DNA and RNA oligomers. For example, PNAs lack 3' to 5' polarity and thus can bind in either a parallel or an antiparallel orientation to DNA or RNA (Egholm, M. et al., *Nature* 365:566, 1993). It has been demonstrated that PNAs can bind double-stranded DNA by invading the DNA duplex and displacing one strand to form a stable D-loop structure (Peffer et al., *Proc. Natl. Acad. Sci. USA* 90:10648, 1993). A further advantage of PNAs is that they are less susceptible to enzymatic degradation (Demidov et al. *Biochem. Pharmacol.* 48:1310, 1994) and bind RNA with higher affinity than analogous DNA oligomers (Norton et al. *Nature Biotechnology* 14:615, 1996). Quite advantageously, selective hybridization of PNA to DNA is less tolerant of base pair mismatches than DNA-DNA hybridization. For example, a single base mismatch within a 16 bp PNA-DNA duplex can reduce the $T_m$ by up to 15° C., compared to 10° C. in the case of a 16 bp DNA-DNA duplex (Egholm, M. et al. *Nature* 365:566, 1993). Finally, in at least one example, a PNA molecule has been shown capable of mimicing a transcription factor and acting as a promoter, thus demonstrating the potential use of PNAs as gene-specific activating agents (Mollegaard et al. *Proc Natl Acad Sci USA* 91:3892, 1994).

The success of an oligonucleotide analog as an antisense drug requires that the oligonucleotide be taken up by cells in large enough quantities to reach its target at a concentration sufficient to cause the desired effect. Until recently PNAs have shown low phospholipid membrane permeability (Wittung et al. *FEBS Letters* 365:27, 1995) and have been reported to be taken up by cells very poorly (Hanvey et al. *Science* 258:1481, 1992; Nielsen et al. *Bioconiugate Chem.* 5:3, 1994; Bonham et al. *Nucleic Acid Res.* 23:1197, 1995), initially suggesting their potential use as anti-gene and anti-sense agents would be quite limited.

Strategies to improve the cellular uptake of PNAs by conjugating the PNA sequence to a carrier molecule have met with some limited success (Basu et al. *Bioconiugate Chem.* 8:481, 1997). Conjugation of PNA molecules to receptor ligand molecules has increased cellular uptake of the PNA; however, the ability of these receptor ligand-conjugated PNA oligomers to influence biological activity once inside the target cells remains unproven. Further, using such a conjugation strategy permits the PNA oligomers to enter only those cells expressing the particular targeted receptor. Thus, an appropriate ligand molecule would have to be designed for each cell type of interest.

However, recently it has been discovered that unconjugated (aka "naked") PNA oligomers administered extracellularly can both cross cell membranes (Gray, G. D. *Biochem. Pharmacol.* 53:1465, 1997) and elicit a sequence-specific biological response in living cells (Richelson, E. *FEBS Letters* 421:280, 1998). Thus, PNAs possess the following characteristics suggesting they are well suited as therapeutic and diagnostic candidates: cell permeability in vivo; higher specificity and stronger binding to its complementary DNA or RNA than oligonucleotides or their analogs; resistance to enzymes like nucleases and proteases thereby showing long biological half-life; chemical stability over a wide pH range; no action as a primer; and an ability to act as a gene promoter.

Improvements in genomic research have increased the rate of generation of information on the identity, structure and function of a number of human genes, thereby producing a diverse group of novel molecular targets for therapeutic and diagnostic applications. However, gene sequencing and characterization is still a slow and often arduous process, as evidenced by the fact that, to date, only a fraction of the entire human genome has been sequenced. The same advantageous binding and chemical stability properties that make PNAs useful as therapeutics and diagnostics also suggest such compounds will be useful in determining the sequence, structure and/or function of DNA and RNA.

In addition to completely characterizing a gene, the tasks of unraveling the details of the interactions of the gene with its DNA binding proteins and determining the mechanisms whereby such proteins mediate gene expression, replication and transduction of the gene require a great deal of time and effort. Further, understanding the genetic malfunctions of dysfunctional genes that cause the many complex genetic disorders found in man still requires extensive research. Thus, here too, PNAs can be useful.

While PNAs appear to be particularly well-suited for use as diagnostics, therapeutics and/or research tools, identification of appropriate PNAS for a specific purpose can be difficult, time consuming and expensive. For example, identifying which region of a gene should be targeted in order to provide a desired effect, such as blocking transcription thereof, or which region, if any, may be activated to promote transcription thereof, generally requires sequencing most, if not all, of the gene and then testing various PNA fragments complementary thereto.

Recently, combinatorial libraries of random-sequence oligonucleotides, polypeptides and/or synthetic oligomers have been employed to facilitate the isolation and identification of compounds capable of producing a desired biological effect or useful as diagnostics. Compounds so identified may mimic or block natural ligands, may interfere with the natural interactions of the target molecule or may simply be useful as tools for designing and developing other molecules with more desirable properties.

Combinatorial libraries useful in this general application may be formed by a variety of solution-phase or solid-phase methods in which mixtures of different subunits are added in a stepwise manner to growing oligomers, until a desired oligomer size is reached. Alternatively, the library may be formed by solid-phase synthetic methods in which beads containing different sequence oligomers that form the library are alternately mixed and separated with one of a selected number of subunits being added to each group of separated beads at each step. An advantage of this method is that each bead contains only one oligomer species, allowing the beads themselves to be used for oligomer screening (Furka, et al., *Int. J. Pept. Protein Res.* 37:487–493 (1991); Sebestyen, et al., *Bioorg. Med. Chem. Letter* 3:413–418 (1993).)

Still another approach that has been proposed involves the synthesis of a combinatorial library on spatially segregated arrays (see, Fodor, et al., *Science*, 251:767–773, 1991). This approach has generally been limited in the number of different library sequences that can be generated.

Because the chance of finding useful ligands increases with the size of the combinatorial library, it is desirable to generate libraries composed of large numbers of different sequence oligomers. For example, in the case of oligonucleotides or oligonucleotide mimics, such as PNAs, a library having a 4-base variability and 8 oligomer residue positions (octamer) will contain $4^8$ (65,536) different sequences to be a complete (universal) library. In the case of a 10 oligomer residue position (decamer) PNA or oligonucleotide universal library, 1,048,576 different sequences must be synthesized.

Because each different-sequence species in a large number library may be present in small amounts, one of the challenges in the combinatorial library screening procedure is isolating and determining the sequence(s) of species that have the desired binding or other selected properties. Thus, not only must the library be universal but the method(s) selected for screening that library must be tailored to distinguish active from non-active species, considering the small amount of each species that is available.

Current methodologies for the synthesis of peptide nucleic acids involve the stepwise addition of suitably protected PNA monomers via one of two standard synthesis protocols. This work has been described in detail in a number of recent papers, including; Dueholm, et al., *J. Org. Chem.*, 59;5767 (1994); Thomson, et al., *Tetrahedron*, 51:6179 (1995); Will, et al. *Tetrahedron*, 51:12069 (1995); Breipohl, et al., *Biorg. Med. Chem. Lett.* 6:665 (1996); Koch, et al., *J. Peptide Res.*, 49:80 (1997); Jordan, S., *Bioorg. Med. Chem. Lett.*, 7:681 (1997); Breipohl, et al., *Tetrahedron*, 53:14671 (1997). More specifically, such methodologies for the synthesis of PNAs involve the stepwise addition of suitably protected PNA monomers generally using one of two standard synthesis protocols. These protocols are based upon the particular protecting group strategy that is used, i.e. either the Fmoc or the Boc-protecting group. The Boc-protecting group strategy requires the use of harsher chemicals and is described in detail in the aforementioned literature. When PNAs are synthesized using the Fmoc-protecting group, typically a solid-phase synthesis resin, for example, a paramethylbenzhydrylamine resin, is used, and the first Fmoc-protected monomer is reacted with the resin using an activating agent, such as HATU, in the presence of a base, such as diisopropylethylamine, and lutidine. After coupling, the reaction mixture is filtered or drained, and the resin is washed. Then unreacted amino groups are generally capped with acetic anhydride to prevent further reaction at those sites. After again washing, the resin-bound monomer is deprotected for the next step of the synthesis by removing the Fmoc-protecting agent using piperidine or the like. Thereafter, this cycle is simply repeated until an oligomer chain of the desired length is obtained, and then cleavage from the resin is effected.

In summary, what is needed are improved, more efficient methods for synthesizing PNAs which can be used to construct such libraries, as well as a system of improved techniques and tools for the rapid identification of agents, particularly PNAs which would be useful in characterizing genes and discovering potential therapeutics and/or diagnostics. In addition to improved PNA synthesis, it would be desirable to be able to efficiently construct libraries which would have the advantages of specificity associated with a large species library, such as an octameric or decameric library, without having to synthesize tens of thousands or millions of different-sequence species. It would also be desirable to have rapid screening methods that may quickly identify "best candidates" from the library for further testing and/or development, and it would be desirable to have a means for determining optimal PNAs, both with respect to sequence base identity and length for use as therapeutics, diagnostics and/or research tools.

SUMMARY OF THE PRESENT INVENTION

The present invention addresses the foregoing and other needs by providing a novel and efficient method for synthesizing activated, protected cyclic intermediates that provide PNA monomers. This novel synthesis adds a solution of a haloacetic acid equivalent to a solution of ethylene diamine and heats to form a cyclic piperazinone. A further reaction is then carried out to add a desired nucleotide base to create cyclic piperazinone intermediates via an amide bond formed with the secondary amino moiety in the piperazinone ring. The remaining amido group in these reaction products is protected with a suitable protecting group to create a piperazinone intermediate that is readily hydrolizable to a peptide nucleic acid monomer and that is readily reactive to form desired derivatives or dimers or other oligomers. The conditions used may also add protection to an unprotected moiety on the base. This novel method provides a rapid, cost-effective and simple approach to the preparation of PNAs using chemical materials that are inexpensive and/or easily prepared.

The invention also provides an overall system involving three key integrated components which permits the rapid identification and/or design of PNAs capable of site-specific recognition of target nucleotide sequences and therefore useful as therapeutics, diagnostics and/or gene characterization tools. One component of this system is a universal PNA library that may be easily and efficiently synthesized and that most preferably has the screening ability of a large library, such as an octameric library, yet does not require synthesis of a large number of individual species. Another component of the overall system is a high throughput screening system, termed the Universal PNA Identification (UPID™) System, that includes a number of assays designed to provide information on the binding activities of PNAs of different sequences relative to the target nucleotide sequence. A third component is a software system especially designed to provide rapid analysis of the data collected from the (UPID™) System and to identify the sequence base identities and lengths of optimal PNA oligomers therefrom.

In one aspect, such a universal library would incorporate universal nucleotide bases into each of the species in order to increase its screening capability without the need for an unmanageable number of individual species. Such a universal library could then be subjected to such an improved high throughput screening process in order to identify novel regulators acting by specific modulation of a selected gene, such as one implicated in a human disease. Optimization of these novel regulators would be guided by such a software system, so as to be capable of predicting the most appropriate therapeutic and/or diagnostic candidates, both in sequence length and sequence base identity. As a result, the structural/functional characterization of newly discovered genes should be enabled, as well as the identification of genomic mutations, such as single nucleotide polymorphisms, in either genomic DNA or PCR-amplified DNA, which would permit genetic diagnosis of disease states as well as the rapid screening of at-risk populations.

BRIEF DESCRIPTION OF THE DRAWINGS

The above and other aspects, features and advantages of the present invention will be more apparent from the following particular description thereof, which is presented in conjunction with the following drawings wherein.

DETAILED DESCRIPTION OF THE PREFERRED EMBODIMENTS

An improved method of PNA synthesis is described hereinafter which utilizes inherently activated piperazinone intermediates which are readily reactive to provide monomers; this strategy provides enhanced recovery of unreacted starting materials, avoids the use of activating agents for each coupling step and reduces the number of additions required for each coupling cycle. As a result, this simplified method significantly reduces the number of separate steps required for each synthesis cycle and thus greatly reduces the cost of synthesizing PNA oligomers.

Figure 1:
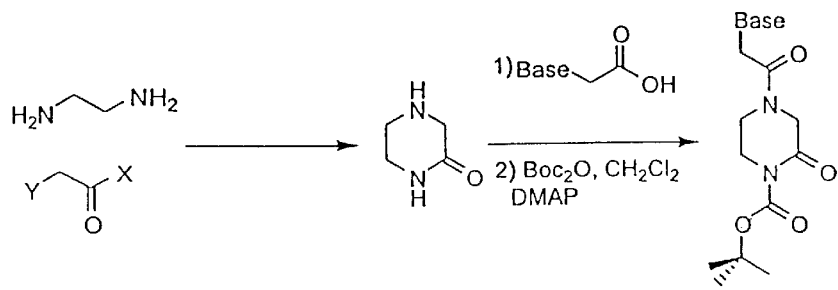
FIG. 1 is a schematic of a synthesis of an activated PNA precursor embodying various features of the present invention.

One synthesis of an inherently activated PNA precursor is presented in FIG. 1. Synthesis begins with the formation of a piperazinone subunit from ethylene diamine and a haloacetic acid equivalent, such as $YCH_2COX$ where X may be hydrogen, halogen or OR, with R being lower alkyl, and Y being halogen or another suitable leaving group. By leaving group is meant a group that will be displaced from the carbon atom during the subsequent reaction, and examples include the halogens and derivatized alcohols, such as inorganic ester groups, e.g. sulfonates and tosylates. Preferably, Y is Br or Cl. Examples include bromoacetic acid, bromomethyl acetate, chloroethyl acetate or bromoacetyl bromide. Slow addition of a solution of, for example, bromoacetic acid, to a solution of ethylene diamine followed by heating gives a desired cyclic piperazinone. Subsequent treatment of the cyclic piperazinone with an activated nucleotide base acetic acid ester provides the desired addition and is followed by protection of the amido group to give a desired base-carrying piperazinone diamide. This protected cyclic intermediate is considered to be a PNA precursor which can easily be hydrolyzed to provide a typical $N^\alpha$Boc-protected PNA monomer. Alternatively, the protected piperazinone intermediate can be used as a pre-activated reagent in a coupling reaction.

Figure 2:
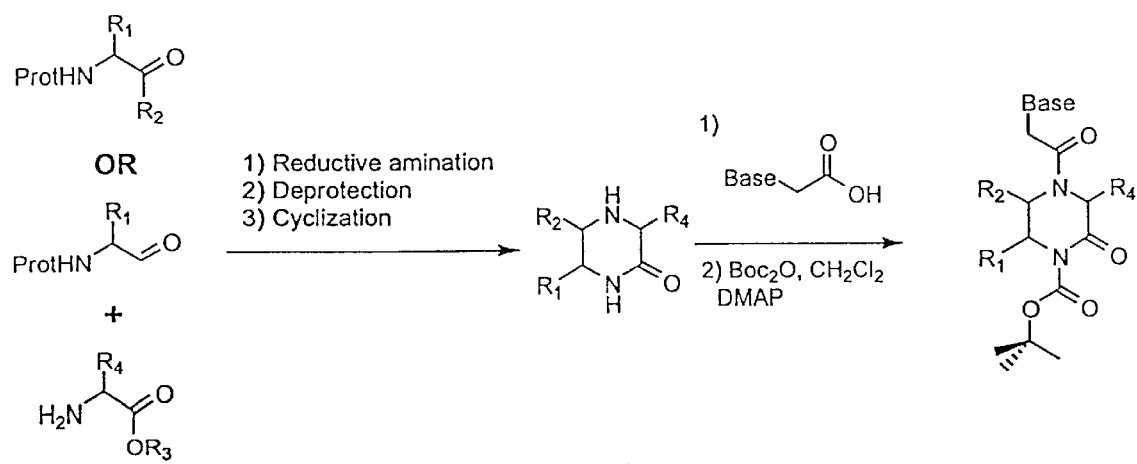
FIG. 2 is a schematic of an alternative synthesis of an activated PNA precursor embodying various factors of the present invention.

As shown in FIG. 2, alternatively, a preactivated, substituted piperazinone intermediate can be prepared using an initial reductive amination reaction between either a protected amino aldehyde or a protected amino ketone and a desired amino acid or equivalent, where $R_1$, $R_2$, $R_3$ and $R_4$ represent hydrogen or any aliphatic, aromatic, substituted aliphatic or substituted aromatic moiety. Subsequent deprotection of the amino group of the original aldehyde or ketone and cyclization give a substituted piperazinone which can then be converted to a pre-activated substituted PNA monomer precursor by reaction with an activated nucleotide base acetic acid ester, as in the synthesis depicted in FIG. 1. The cyclic substituted piperazinone intermediate serves as a PNA precursor that can be similarly easily hydrolyzed to give the $N^\alpha$-Boc protected free acid PNA monomer, or it may be utilized as a pre-activated coupling reagent to which a nucleophile can be added to yield a desired product.

Figure 3:
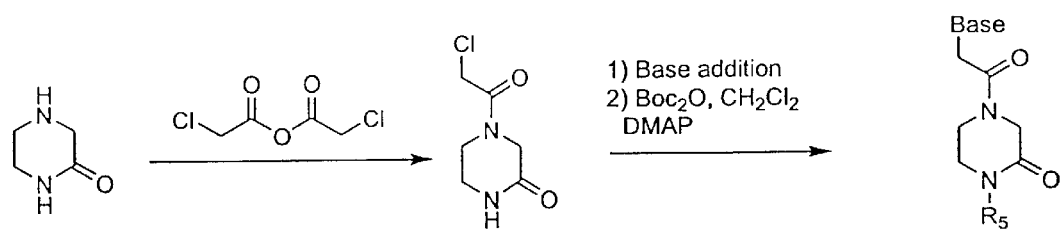
FIG. 3 is a schematic of an alternative synthesis to that depicted in FIG. 1.

An alternative approach to the preparation of such an inherently activated PNA precursor is presented in FIG. 3. In many cases, this approach provides significant advantages over the syntheses described above. By coupling a modified piperazinone directly with a nucleotide base, one avoids having to perform an activated ester coupling with a nucleotide base acetic acid, and the purification of the reaction product becomes significantly easier. Additionally, the total number of steps in the synthesis of each PNA precursor are reduced, and in many cases, higher yields are obtained. Because the starting materials are all readily available in large quantities, the chloroacetyl-piperazinone intermediate shown in FIG. 3 can be easily prepared in large scale. The piperazinone that is the product of the first reaction depicted in FIG. 1 is treated with chloroacetic anhydride or an equivalent acylating agent, such as chloroacetyl acid chloride, to provide chloroacetyl-piperazinone. This modified piperazinone can then be treated directly with the desired nucleotide base (a purine, pyrimidine, or other protected base, e.g. a universal base) under basic conditions to produce the illustrated piperazinone intermediate where $R_5$ is H. Reaction with Boc-anhydride (di-t-butyl dicarbonate) yields the protected pre-activated PNA precursor where $R_5$ is Boc; examples of other preferred protecting groups include benzyl chloroformate and 2-nitrobenzenesulfonyl chloride. Although Boc (t-butyloxycarbonyl) is preferably used as the amido-protecting agent, suitable carbamate, acyl and sulfonyl protecting groups may be used, as well as other suitable groups from the large collection of known α-amino protecting groups used in solid-phase peptide synthesis.

Figure 4:
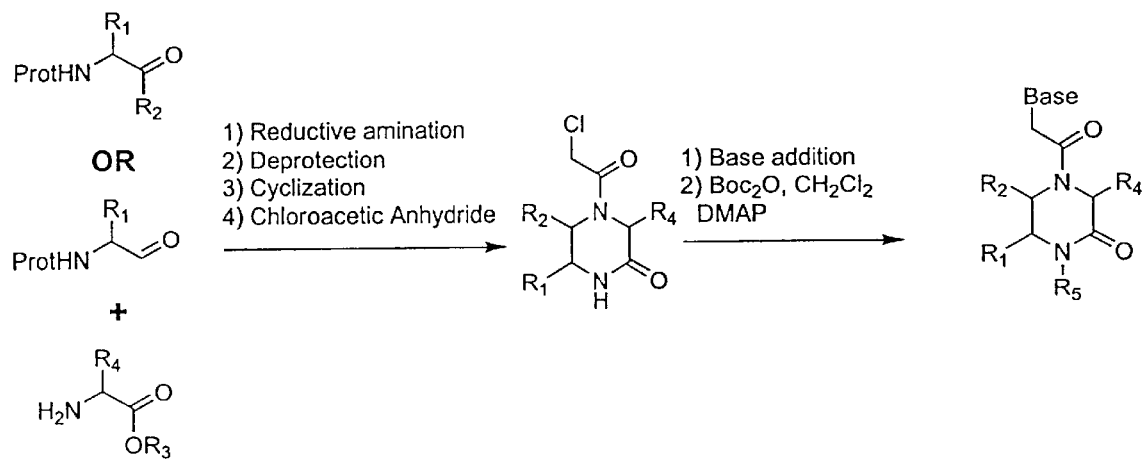
FIG. 4 is a schematic of an alternative synthesis to that depicted in FIG. 2.

In a similar fashion, more highly substituted precursors can be prepared by beginning with a reductive amination reaction between an amino aldehyde or amino ketone and an amino acid or a derivative thereof as depicted in FIGS. 2 and 4, followed by deprotection and cyclization to create the substituted piperazinone. Then, either reaction with an activated nucleotide base acetic acid ester (as in FIG. 2), or acylation with chloroacetic anhydride or an equivalent acylating agent (as in FIG. 4) to produce the chloroacetyl-substituted piperazinone, which is then directly converted to the desired piperazinone intermediate by coupling with the desired nucleotide base under basic conditions, produces the intermediate wherein $R_5$ is H. Protection of the amido group in the piperazinone ring then gives the desired precursor as in FIG. 1. With such protection in place, the ring-opening reaction proceeds without undesirable side reactions.

More specifically, the reductive amination reactions depicted in FIGS. 2 and 4 involve an initial reaction between either an amino aldehyde having the formula PHN—CHR—CHO or an amino ketone having the formula PHN—$CHR_1$—C(=O)—$R_2$ and an α-amino acid or ester having the formula $H_2N$—$CHR_4$—$COOR_3$. In the reductive amination reaction, an imine is formed between the primary amino group of the amino acid and the carbonyl group of the aldehyde or ketone, which is then reduced to an amine by treatment under reducing conditions with an agent such as sodium cyanoborohydride. Thereafter, the amino group of the aldehyde or ketone is deprotected, and heating under conditions similar to those used in the reaction depicted in FIG. 1, e.g. 4 to 5 hours under reflux conditions, produces the piperazinone intermediate as illustrated in FIG. 2. P represents any amino-protecting group, such as Boc. $R_1$, $R_3$ and $R_4$ may be hydrogen, lower alkyl, substituted lower alkyl or aromatic. Common substitutions such as halogen, nitro or alkoxy may be used, with phenyl and benzyl being the most common aromatic substituents. $R_2$ would be lower alkyl, e.g. methyl or ethyl, substituted lower alkyl or aromatic. For example, alanine might be reacted with amino acetaldehyde or with amino acetone or with amino methyl ethyl ketone to provide such a substituted piperazinone intermediate.

The syntheses briefly described above provide simple and cost-effective methods of preparing variably substituted pre-activated PNA precursors. Certain of these methods are outlined in greater detail in the specific examples which follow that should provide a better understanding of this aspect of the invention. In these specific examples, reagents and solvents were obtained from commercial sources and used without further purification unless indicated. Dichloromethane and toluene were dried over 4-angstrom molecular sieves prior to use. The following abbreviations are used: NaOEt, Sodium ethoxide; EtOH, Ethanol; MeOH, Methanol; DMF, Dimethylformamide; DMAC, N,N-Dimethylacetamide; DIEA, N,N'-Diisopropylethylamine; DIC, 1,3-Diisopropylcarbodiimide; DCM, Dichloromethane; HOBt, N-Hydroxybenzotriazole monohydrate; DMAP, 4-Dimethylaminopyridine; $Boc_2O$, Di-t-butyl dicarbonate; EtOAc, Ethylacetate; $NEt_3$, Triethyl amine; LiH, Lithium hydride; LiOH, Lithium Hydroxide; NMP, N-methylpyrrolidinone; $K_2CO_3$, Potassium carbonate; Cbz, Benzyloxycarbonyl; Bz, Benzoyl. All products were characterized by NMR, mass spec., and HPLC although other analytical methods may have been utilized where appropriate.

EXAMPLE 1

Piperazinone Synthesis

Ethylene diamine (245 mmol, 16.37 mL) was dissolved in dry EtOH (75 mL) under $N_2$ with vigorous stirring. A solution of ethyl chloroacetate (40.8 mmol, 5 g) in EtOH (25 mL) was added dropwise over 2 hours and stirring was continued for an additional 22 hours. After 22 hours stirring, 1 equivalent of NaOEt was added to the reaction mixture (prepared from 938 mg sodium metal in 45 mL ethanol) with continued rapid stirring for an additional 2 hours. The milky solution was filtered through a 1-inch plug of celite, and the filter cake was washed with ethanol (3×10 mL). The combined organic phase was concentrated by rotary evaporation to remove both the ethanol and the excess diamine. The crude oil was treated with toluene (250 mL) and heated to reflux for 4 hours. The toluene layer was decanted off while still hot and then allowed to gradually cool to room temperature. The remaining oil was again treated with 250 mL of toluene and heated to reflux for an additional 3 hours, and the toluene phase was decanted into an Erlenmeyer flask and allowed to cool to room temperature. The two toluene phases were held at −4° C. overnight to crystallize. The crystalline product was collected, washed twice with ice cold toluene, and then dried under vacuum to afford 3.23 g of piperazinone as a pale golden solid (by NMR, about 85% pure). Further purification was accomplished by an additional recrystallization from acetone and hexane. The crude solid mass was dissolved in a minimum volume of hot acetone. After dissolution was complete, the hot acetone solution was titurated with hexane until the solution became cloudy. The solution was boiled until complete dissolution was observed; then it was allowed to slowly cool to room temperature and stored at −4° C. overnight. The resulting fine pale yellow crystals were collected by vacuum filtration and dried under vacuum yielding the piperazinone as a pale yellow free-flowing solid (>95% pure, 65% overall yield).

EXAMPLE 2

Chloroacetyl-piperazinone Synthesis

Anhydrous piperazinone (10 mmoles, 1.002 g) was suspended in dry DCM (100 mL) under nitrogen atmosphere and treated with chloroacetic anhydride (11 mmoles, 1.88 g). The reaction mixture was stirred at room temperature for 3 hours and treated with 3 equivalents of tris-amine resin (6 mmol/g, 5 g) to sequester the unreacted chloracetic acid. After stirring an additional 5 minutes, the reaction mixture was filtered, and the resin was washed with DCM (3×100 mL). The solvent was removed by rotary evaporation, and the resulting oil was treated with EtOAc. The resulting precipitate was collected by filtration to afford the desired chloroacetyl-piperazinone, as a cream-colored solid in 95% yield (1.68 g).

EXAMPLE 3

N-(Thymin-1-ylacetyl)piperazinone Synthesis Using Method of FIG. 1

A 0.6 M solution of thymine-1-acetic acid (440 mg/4 mL) in DMF was treated with 1.5 mL of 3.2 M DIC in DMF. The reaction mixture was stirred at room temperature for 2–3 minutes and treated with 1.1 equivalents of piperazinone (263 mg) as prepared in Example 1. Stirring was continued for approximately 48 hours, and the solvent was removed by rotary evaporation. The residue was washed extensively with ethyl acetate to remove the diisopropyl urea, and the white solid mass was collected by filtration. An additional wash with 1:9, methanol:DCM removes any unreacted thymine-1-acetic acid, resulting in an 80% yield of pure unprotected piperazinone intermediate as a white solid.

EXAMPLE 4

N-(Thymin-1-ylacetyl)-piperazinone Synthesis Using Method of FIG. 3

Thymine (630.6 mg, 5 mmol) and $K_2CO_3$ (1.38 g, 10 mmol) were combined in a 50 mL round bottom flask and azeotroped with benzene (3×10 mL). The mixture was suspended in anhydrous DMF (15 mL) under argon and allowed to stir at room temperature for 4 hours. Solid chloroacetyl piperazinone (1.37 mmol, 1.4 eq) as prepared was added, and the reaction mixture was stirred for an additional 3–4 hours. The crude reaction mixture was filtered, concentrated and precipitated by treatment with EtOAc (30 mL). The solid was washed extensively with EtOAc and dried in a dessicator under vacuum to afford 1.33g of N-(thymin-1-ylacetyl)-piperazinone (100% yield) as a white solid.

EXAMPLE 5

Preparation of the Inherently Activated Thymine PNA Precursor 5.5 g, of N-(thymin-1-ylacetyl)-piperazinone (20.6 mmol) was suspended in 200 mL of dry DCM and treated with 3.77 g (1.5 eq, 30.9 mmol) DMAP, 11.23 g (51.5 mmol, 2.5 eq) Boc-anhydride and 7.2 mL (51.5 mmol, 2.5 eq) of triethylamine. The reaction also results in protection of the secondary amino group on the thymine. The reaction mixture was stirred at room temperature for 3–4 hours, while following the reaction progress by TLC. Upon completion, the reaction mixture was concentrated by rotary evaporation, and the resulting oil was resuspended in DCM. The organic phase was washed successively with 0.1 N HCl solution (2×25 mL), water (2×100 mL) and dried over sodium sulfate. Concentration and purification by recrystallization from diethyl ether afforded 6 g of the Boc-protected thymine PNA precursor (80% yield) as a white solid.

EXAMPLE 6

Synthesis of N-[(N4-(CBz-cytosine-1-yl)acetyl]-piperazinone: Using the Method of FIG. 1

($N^4$-CBz-cytosin-1-yl)acetic acid (2.42 g, 8 mmol) was azeotroped with benzene (3×25 mL) and dried under vacuum. 32 mL of anhydrous DMF was added under $N_2$ followed by the addition of DIC (1.57 mL, 8 mmol). The reaction was stirred at room temperature for 2–3 minutes, then treated with piperazinone (8.8 mmol, 881.1 mg), and the reaction mixture was left to stir for 48 hours. The reaction mixture was concentrated by rotary evaporation, washed successively with 0.1 N citric acid solution (2×10 mL) and water (2×15 mL), and then dried in a dessicator, affording N-[($N^4$-CBz-cytosin-1-yl)acetyl]-piperazinone as a white solid.

EXAMPLE 7

Synthesis of the Bis-Boc Protected CBz-cytosine PNA Precursor

N-[($N^4$-CBz-cytosin-1-yl)acetyl]-piperazinone (1 g, 2.595 mmol) was suspended in 100 mL of DCM under argon and treated with DMAP (793 mg, 6.488 mmol). Boc-anhydride (1.42 g, 6.488 mmol) was added, followed by 0.862 mL (6.488 mmol, 2.5 eq) of triethylamine. The reaction mixture was stirred at room temperature for 4 hours and then concentrated by rotary evaporation; thereafter, the product was precipitated with ether to give 911 mg of the bis-Boc protected CBz-cytosine PNA precursor as a white solid (60% yield).

EXAMPLE 8

Synthesis of N-[($N^4$-CBz-cytosine-1-yl)acetyl]-piperazinone: Using the Method of FIG. 3

$N^4$-Benzoylcytosine (204 mg, 0.98 mmol) was suspended in anhydrous DMF (30 mL) with $K_2CO_3$ (298 mg, 2.2 mmol) and stirred at room temperature for 1 hour. Solid chloroacetyl piperazinone (1.37 mmol, 1.4 eq) was added, and the reaction mixture was stirred for an additional 34 hours. The reaction mixture was filtered and concentrated to afford the crude product. Recrystallization from methanol and acetone (7:3) at 4° C. overnight gave N-[($N^4$-Bz-cytosin-1-yl)acetyl]-piperazinone as a solid white product. It was collected by filtration, washed with DCM and methanol and dried to afford 288 mg (86% yield).

EXAMPLE 9

Synthesis of the Mono-Boc and Bis-Boc Protected Benzoyl-cytosine PNA Precursors 212 mg of N-[($N^4$-Bz-cytosin-1-yl)acetyl]-piperazinone monomer was suspended in DCM and treated with DMAP (1.0 eq, 73 mg), Boc-anhydride (1.2 eq, 156 mg) and triethyl amine (1.2 eq, 100 µL). The reaction mixture was stirred at room temperature for 2.5 hours, then treated with additional Boc-anhydride (1.2 eq, 156 mg) and triethyl amine (1.2 eq, 100 µL). The major product, the mono-Boc-protected precursor, was collected by filtration, washed with DCM and dried to afford a pure product (60% yield). The remaining solution containing the bis-Boc-protected monomer was concentrated by rotary evaporation, and the resulting oil was resuspended in DCM. The organic phase was washed with 0.1 N HCl solution (2×2.5 mL), water (2×5 mL) and dried over $Na_2SO_4$. Concentration and purification by recrystallization from diethyl ether affords the pure Bis-Boc-protected PNA precursor (25% yield). Both precursors are inherently activated, and the amido group in the piperazinone ring is protected by Boc; either can be used in any of the derivatization or oligomerization reactions hereinbefore described.

EXAMPLE 10

Synthesis of (Adenine-$N^9$-acetyl)-piperazinone: Using the Method of FIG. 3

Adenine (1.5 g, 11.1 mmol) was azeotroped three times with toluene (10 mL each time) and suspended in anhydrous DMF (60 mL) under argon. Sodium hydride (293 mg, 12.2 mmol) was added, and the reaction mixture was heated to 80° C. and allowed to stir for 20 min. Chloroacetyl-piperazinone (1.2 eq, 13.3 mmol) was added, and the reaction mixture was stirred vigorously for 2 hours at 80° C. The resulting solution was cooled and filtered to afford the desired (Adenine-$N^9$-acetyl)-piperazinone in 80% yield. Additional product can be isolated from the remaining solution. Thus, the solution was evaporated to dryness, redissolved in methanol and stored at 4° C. overnight. The solid product was collected by filtration and dried under vacuum, affording (Adenine-$N^9$-acetyl)-piperazinone as a white solid. The combined materials give a 90% total yield of the desired intermediate.

EXAMPLE 11

Preparation of the Boc Protected Adenine PNA Precursor (Adenine-$N^9$-acetyl)-piperazinone (3 g) was suspended in anhydrous DMF (80 mL) under argon and treated with 2.66 g (21.8 mmol) DMAP. Next, 8.32 g (38.2 mmol) of Boc-anhydride and 5.3 mL (38.2 mmol) triethylamine were added, and the reaction mixture was left to stir at room temperature for 2 hours. An additional 3.5 equivalents of Boc-anhydride and 3.5 equivalents of triethylamine were added, and the reaction mixture was left to stir for an additional 3–4 hours. The solvent was removed by rotary evaporation, and the crude material was redissolved in DCM and washed with 0.1 N HCl solution (50 mL) and water (2×100 mL). The organic phase was dried over $Na_2SO_4$, filtered and concentrated. Purification by column chromatography with 3:1 ethyl acetate in hexane afforded the desired tris-Boc-protected PNA precursor in 56% overall yield.

EXAMPLE 12

Synthesis of 2-N-Acetyl-6-O-diphenylcarbamoyl-guanine-9-N acetyl-piperazinone: Using the Method of FIG. 2

2-N-Acetyl-6-O-diphenylcarbamoyl-guanine (2.57 mmol, 1 g) was dissolved in anhydrous DMF (10 mL) under nitrogen and treated with 2.5 equivalents (6.425 mmol, 888 mg) of anhydrous potassium carbonate. The suspension was stirred at room temperature for 0.5 hours and then treated with solid chloroacetyl-piperazinone (3.86 mmol, 682 mg). Stirring was continued for 6 hours. The solvent was removed under reduced pressure, and the resulting solid was redissolved in methanol. The solution was placed in the 4° C. refrigerator overnight, and 1.033 g of 2-N-Acetyl-6-O-diphenylcarbamoyl-guanine was obtained as a solid white precipitate (76% yield).

EXAMPLE 13

Preparation of the Inherently Activated Guanine PNA Precursor

The Guanine intermediate from Example 12 (540 mg, 1.02 mmol) was placed in a 100 mL round bottom flask with DMAP (191.3 mg, 1.53 mmol) and suspended in DCM (60 mL) under argon. Triethylamine was added (338 μmL, 2.55 mmol), followed by Boc-anhydride (570 mg, 2.55 mmol). After stirring at room temperature for 4 hours, the reaction mixture was washed with 0.1N HCl solution and concentrated by rotary evaporation. The resulting orange oily solid was purified by chromatography using ethyl acetate as eluent, affording an 80% yield of the bis-Boc protected guanine PNA precursor.

Modification and Oligomerization Reactions Utilizing the Inherently Activated Piperazinone Monomers The inherently activated PNA precursors described above provide improved and more efficient methods of PNA oligomer synthesis as described hereinafter. There are several key advantages afforded by this strategy of PNA oligomer synthesis. The use of these inherently activated precursors provides enhanced recovery of unreacted starting materials, minimizing waste. The use of activating agents for the various coupling steps is completely avoided, and the number of additions required for each coupling cycle is reduced. The protecting group strategy is simplified because oligomerization is very selective for the terminal aliphatic amino group of the growing PNA chain so that protection of amino or amido groups linked to or a part of an aromatic ring becomes unimportant. Easy acquisition of C-terminally modified PNA monomers or oligomers, as well as traditional Boc-PNA monomers, is provided.

The inherently activated PNA precursors are very stable to a variety of conditions and can be stored in solution for periods ranging from several days to several weeks without significant decomposition as long as nucleophiles are not present. Because no additives or coupling reagents are needed during the coupling steps, it is possible to recover essentially all of the unreacted precursor. This significantly reduces the cost of solid phase synthesis when such excess reagent can be easily recovered after completion of the reaction. The ring-opening reaction itself is highly selective. In several coupling studies, even when all protecting groups were removed from a resin-bound PNA monomer, coupling was observed to occur only at the terminal aliphatic amine. This allows for the use of simple and inexpensive protecting groups in the formation of the PNA precursors because loss of a protecting group during the oligomerization reaction does not normally lead to formation of undesired side products, such as multiple addition products. Additionally, the inherently activated PNA precursors can be treated with any nucleophile, e.g. amine, alcohol, thiol, etc., to provide various C-terminally modified derivatives when desired. Moreover, the use of a base, such as lithium hydroxide, as the nucleophile provides the more standard Boc-protected PNA monomers, as shown in the examples which follow.

EXAMPLE 14

Figure 5:
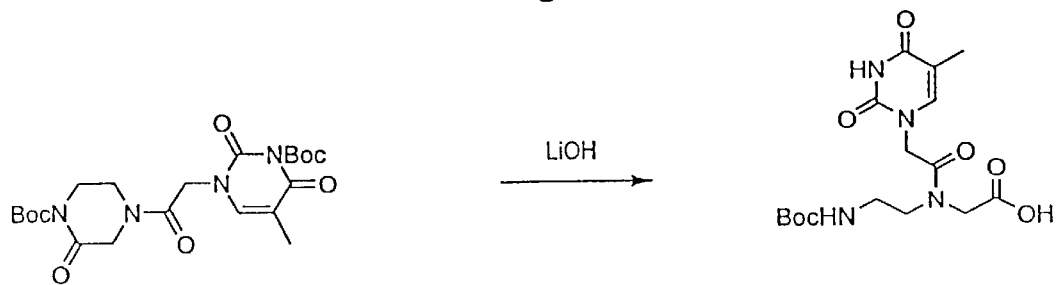
FIGS. 5–8 schematically show the hydrolysis of cyclic piperazinone intermediates to protected PNA monomers.

An example of the ring-opening reaction of the inherently activated T precursor with lithium hydroxide (LiOH) is depicted in FIG. 5.

10 mg (0.0215 mmol) of protected thymine precursor of Example 5 was treated with 0.95 mL of a 6:1 mixture of tetrahydrofuran (THF) and 1N LiOH. Immediately after the addition is complete, the reaction mixture is concentrated to ⅛th of its original volume and acidified to pH 4 with 1N HCl solution. Precipitation with ether affords the protected PNA monomer in quantitative yield.

EXAMPLE 15

Figure 6:
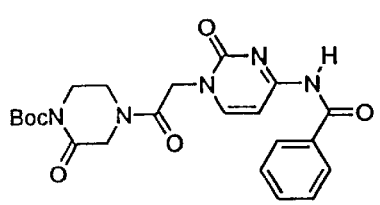
Figure 6:
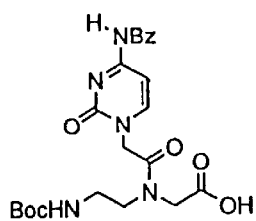

An example of the ring-opening reaction of the inherently activated C-precursor from Example 9 with lithium hydroxide is depicted in FIG. 6.

5 mg (9 μmol) of the protected C-precursor of Example 9 was treated with 0.125 mL of a 6:1 mixture of THF and 1N LiOH. Immediately after the addition is complete, the reaction mixture is concentrated to ⅙th of its original volume and acidified to pH 4 with 1N HCl solution. Precipitation with ether affords the protected PNA monomer in quantitative yield.

EXAMPLE 16

Figure 7:
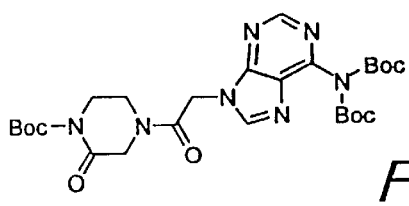
Figure 7:
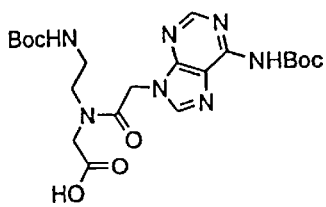

An example of the ring-opening reaction of the inherently activated A precursor and lithium hydroxide is depicted in FIG. 7.

15 mg (0.0261 mmol) of the protected A precursor of Example 11 was treated with 0.365 mL of a 6:1 mixture of THF and 1N LiOH. Immediately after the addition is complete, the reaction mixture is concentrated to ⅙$^{th}$ of its original volume and acidified to pH 4 with 1N HCl solution. Precipitation with ether affords the adenine PNA monomer in 95% yield.

EXAMPLE 17

Figure 8:
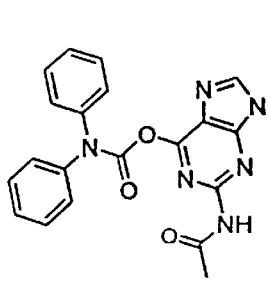
Figure 8:
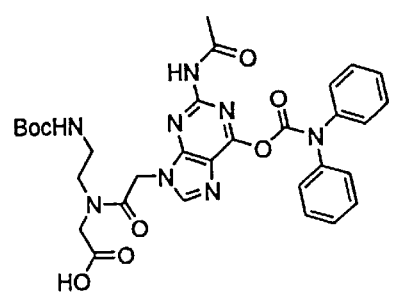

An example of the ring-opening reaction of the inherently activated G precursor with acetyl protection on the pendent primary amino group and lithium hydroxide is depicted in FIG. 8.

20 mg of the protected G precursor of Example 13 (0.0274 mmol) was treated with 0.400 mL of a 6:1 mixture of THF and 1N LiOH. Immediately after the addition is complete, the reaction mixture is concentrated to ⅙th of its original volume and acidified to pH 4 with 1N HCl solution. Precipitation with ether affords the guanine PNA monomer in 90% yield. (Some material was lost due to the occurrence of some removal of the 6-O-diphenylcarbamoyl protecting group.)

Below are several examples highlighting the utility of these precursors in providing PNA monomers for various syntheses. In order to better understand these examples, please refer to FIGS. 11–19. The ring-opening reaction presented below works extremely well in both solution-phase (see Examples 18–19) and in solid-phase reactions (see Examples 20–31). The reaction proceeds well in most solvents (for example, toluene, NMP, dimethyl sulfoxide (DMSO), tetrahydrofuran, 1,4-dioxane and DCM); however, it proceeds faster in polar aprotic solvents such as DMF, DMSO or NMP (see Examples 14 and 15), or protic solvents such as water (see Examples 16–19). This ring-opening reaction can be used for the formation of PNA oligomers, as demonstrated by the formation of the PNA tetramer in Example 29, and such PNA oligomers of greater length (up to about 20 bases) can be readily prepared by this method.

EXAMPLE 18

Figure 9:
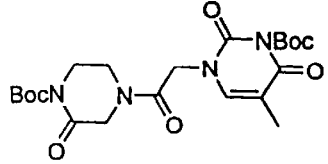
FIGS. 9 and 10 show examples of nucleophilic attack of a protected PNA precursor to provide a C-terminally modified PNA monomer.
Figure 9:
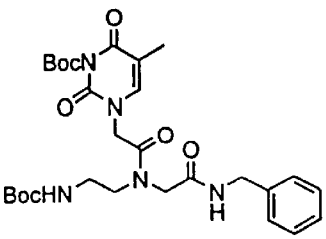

A reaction with benzyl amine provides a simple example of the ring-opening reaction of the inherently activated T precursor of Example 5 and is depicted in FIG. 9. This reaction is indicative of the ability of the precursor to readily couple with nucleophiles to provide C-terminally modified PNA monomers.

10 mg (0.0215 mmol, 2 eq) of the inherently activated T precursor was dissolved in anhydrous DMF and treated with 1 equivalent of benzylamine (1.2 μL, 0.0107 mmol). After stirring at room temperature for 1 hour, he reaction mixture was concentrated and purified to afford the PNA amide shown as a pale yellow solid in 83% yield (10.4 mg).

EXAMPLE 19

Figure 10A:
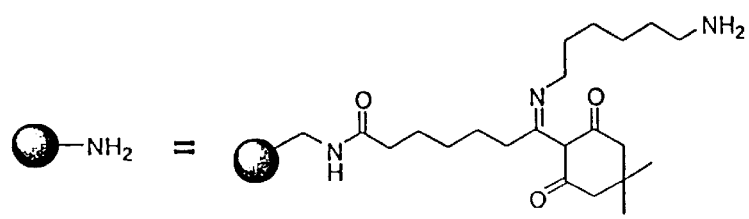
FIG. 10A schematically illustrates a specialized resin used for solid-phase synthesis reactions as described with respect to FIGS. 11–18.
Figure 10:
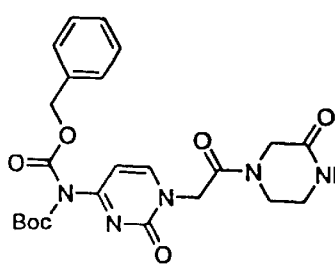
Figure 10:
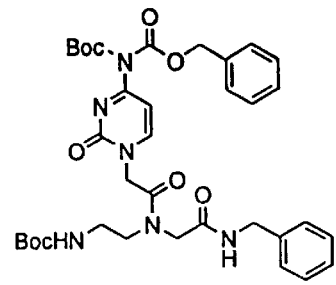

A similar example of the ring-opening reaction of the inherently activated C precursor and benzylamine is depicted in FIG. 10.

20 mg (0.0339 mmol, 1 eq) of the inherently activated precursor of Example 7 was dissolved in a mixture of anhydrous DMF and DCM (1:5, just enough DMF to dissolve the precursor) and treated with 3 equivalents of benzylamine (11 μL, 0.1016 mmol). After stirring at room temperature for 8 hours, the reaction mixture was concentrated and purified to afford the PNA amide shown as a white solid in 89% yield (21.1 mg).

EXAMPLE 20

Figure 11:
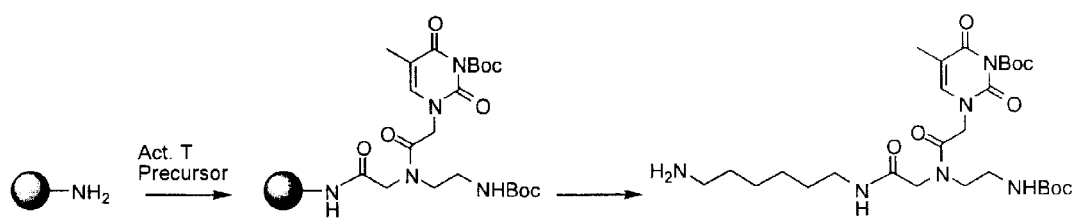
FIG. 11–15 are schematics of the attachment of five different activated piperazinone intermediates to the resin of FIG. 10A followed by the subsequent cleavage from the resin (to illustrate the results at the C-terminus following completion of synthesis of the desired oligomer)

An example of the ring-opening reaction of the inherently activated T precursor with a resin-bound nucleophile is depicted in FIG. 11.

30 mg of CLEAR-DDE-hexamethylene diamine resin (0.4 mmol/gm) (see FIG. 10A) was placed in 2 mL reaction vessel and preswelled with NMP for 20 min. A stock 0.2 M solution of Boc-protected thymine precursor of Example 5 was prepared in anhydrous NMP, and 3 equivalents (180 μL) of the precursor was added to the swollen resin. The reaction mixture was stirred at room temperature for 1 hour, then drained. The resin reaction product, which is shown, was washed 3 times with NMP and then 3 times with DCM and allowed to dry. The dried material was treated with 1.5 mL of a 2% hydrazine solution in MeOH for 1 hour to cleave the reaction product, and the solution was collected. This cleavage process was repeated, and the combined organic solutions were dried to provide, as a single product, the PNA monomer shown including the desired hexylamine linker as an α-amino alkyl amide at the C-terminus.

EXAMPLE 21

Figure 12:
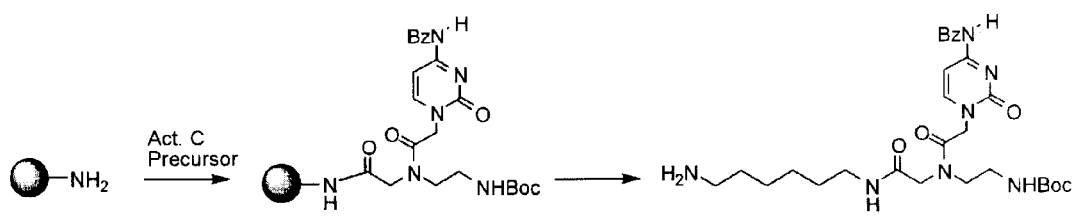

An example of the ring-opening reaction of the inherently activated C precursor with a resin-bound nucleophile is depicted in FIG. 12.

30 mg of CLEAR-DDE-hexamethylene diamine resin (0.4 mmol/gm) was placed in 2 mL reaction vessel and preswelled with NMP for 20 min. A stock 0.2 M solution of cytosine precursor of Example 9 was prepared in anhydrous NMP, and 3 equivalents (180 μL) of the precursor was added to the preswelled resin. The reaction mixture was stirred at room temperature for 1 hour and then drained. The resin reaction product, which is shown, was washed 3 times with NMP, and 3 times with DCM. The dried material was treated with 1.5 mL of a 2% hydrazine solution in MeOH for 1 hour, and the solution was collected. This cleavage process was repeated, and the combined organic solutions were dried to provide, as a single product, the PNA monomer shown having the C-terminal linker as an alkyl amide.

EXAMPLE 22

Figure 13:
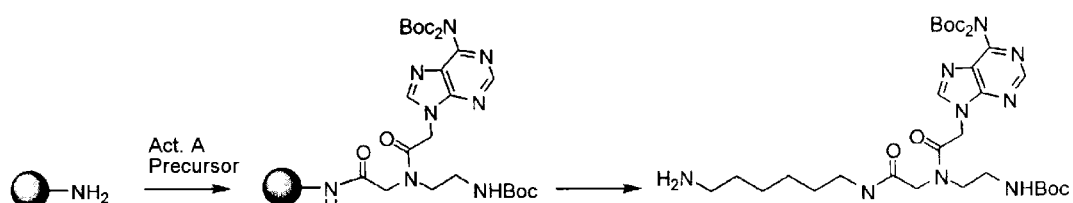

An example of the ring-opening reaction of the inherently activated A precursor with a resin-bound nucleophile is depicted in FIG. 13.

30 mg of CLEAR-DDE-hexamethylene diamine resin was placed in 2 mL reaction vessel and preswelled with NMP for 20 min. A stock 0.2 M solution of Boc-protected adenine precursor of Example 11 was prepared in anhydrous NMP, and 3 equivalents (180 μL) of the monomer was added to the swollen resin. The reaction mixture was stirred at room temperature for 1 hour and then drained. The resin reaction product, which is shown, was washed 3 times with vvvvvvvvvvvvvvvvNMP, and 3 times with DCM. The dried material was treated with 1.5 mL of a 2% hydrazine solution in MeOH for 1 hour, and the solution was collected. This cleavage process was repeated, and the combined organic solutions were dried, to provide, as a single product, the PNA monomer shown including the C-terminal linker as an alkyl amide.

EXAMPLE 23

Figure 14:
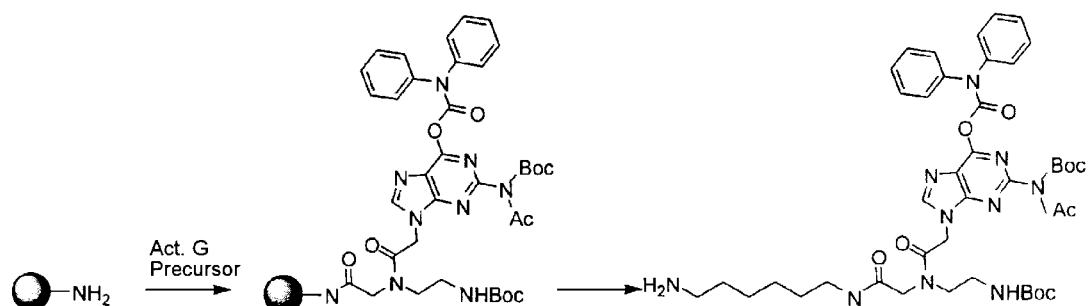

An example of the ring-opening reaction of the inherently activated G precursor with a resin-bound nucleophile is depicted in FIG. 14.

30 mg of CLEAR-DDE-hexamethylene diamine resin was placed in 2 mL reaction vessel and preswelled with NMP for 20 min. A stock 0.2 M solution of Boc-protected guanine precursor of Example 13 was prepared in anhydrous NMP, and 3 equivalents (180 μL) of the monomer was added to the swollen resin. The reaction mixture was left to stir at room temperature for 1 hour, then drained. The resin reaction product, which is shown, was washed 3 times with NMP, and 3 times with DCM. The dried resin was treated with 1.5 mL of a 2% hydrazine solution in MeOH for 1 hour, and the solution was collected. This cleavage process was repeated, and the combined organic solutions were dried to provide, as a single product, the PNA monomer shown including the C-terminal linker as an alkyl amide.

EXAMPLE 24

Figure 15:
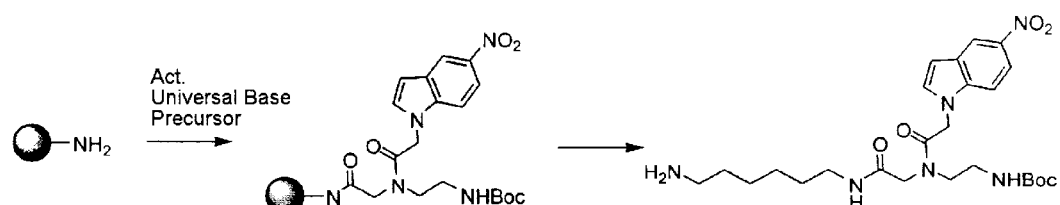

An example of the ring-opening reaction of an inherently activated Universal base precursor with a resin-bound nucleophile is depicted in FIG. 15.

A Boc-protected universal base precursor is synthesized using the same general strategy as set forth in Examples 12 and 13, but using N-acetyl-5-nitroindole as the base.

30 mg of CLEAR-DDE-hexamethylene diamine resin was placed in 2 mL reaction vessel and preswelled with NMP for 20 min. A stock 0.2 M solution of the Boc-protected universal base precursor was prepared in anhydrous NMP, and 3 equivalents (180 μL) of the precursor was added to the swollen resin. The reaction mixture was stirred at room temperature for 1 hour and then drained. The resin reaction product, depicted in FIG. 15, was washed 3 times with NMP, and 3 times with DCM. The dried material was treated with 1.5 mL of a 2% hydrazine solution in MeOH for 1 hour, and the solution was collected. This cleavage process was repeated, and the combined organic solutions were dried to afford the monomer shown, including the desired C-terminal linker, as a single product.

EXAMPLE 25

Figure 16:
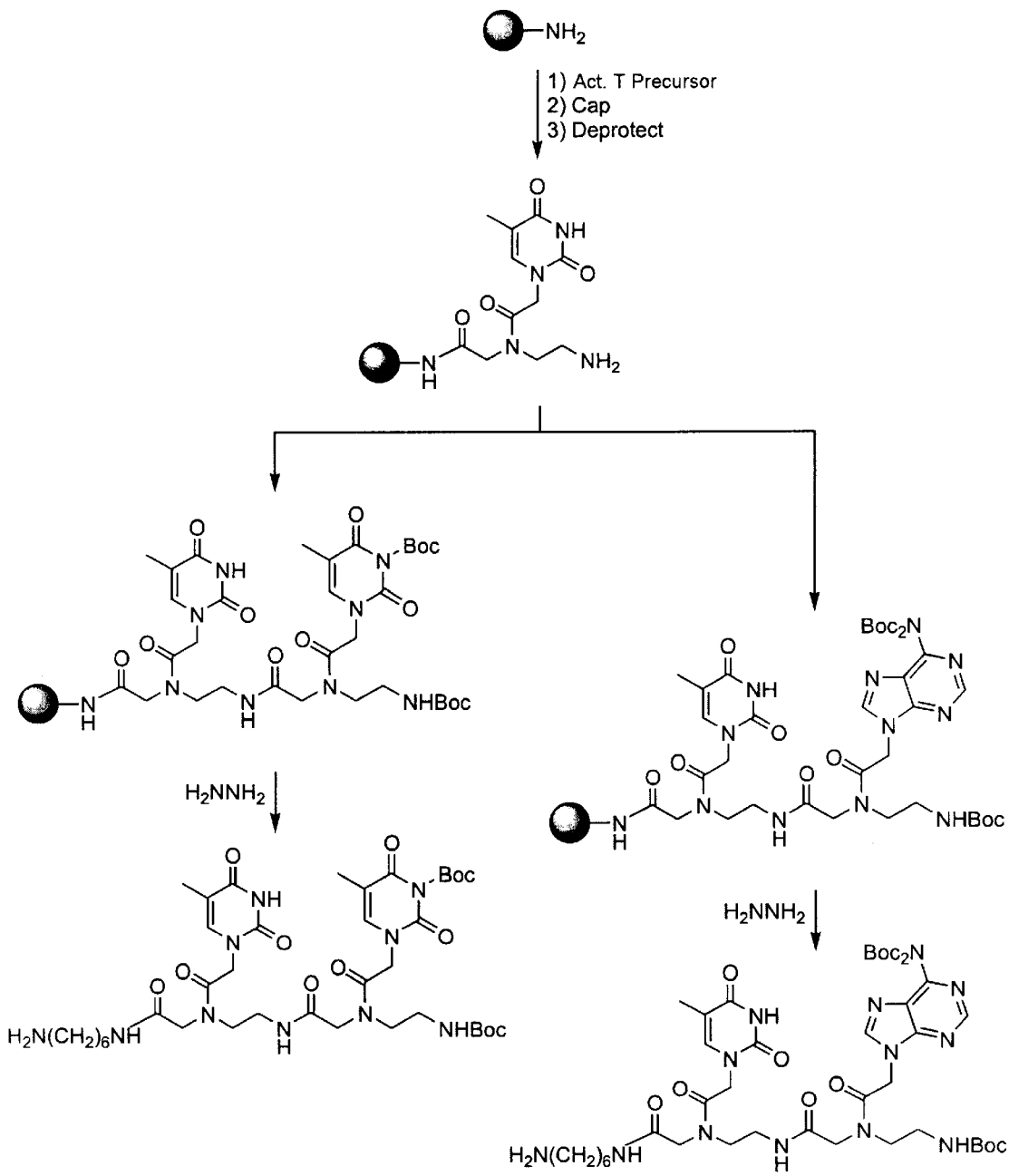
FIG. 16 is a schematic showing two parallel syntheses for creating PNA dimers with a desired linker at the C-terminus embodying various features of the invention.

Solid phase synthesis of PNA dimers as depicted in FIG. 16.

40 mg of CLEAR-DDE-hexamethylene diamine resin was placed in 2 mL reaction vessel and preswelled with 1 mL NMP for 20 min; then the solution was drained. A stock 0.2 M solution of thymine precursor from Example 5 was prepared in anhydrous NMP, and 3 equivalents of the precursor were added to the swollen resin, as in Example 20. The reaction mixture was stirred at room temperature for 1 hour and then drained. The resin reaction product was washed 3 times with NMP; it was then treated with a capping solution of 1 M NEt$_3$ and 0.5 M acetic anhydride in NMP (500 μL) for 5 minutes and then drained. The capped resin reaction product was thereafter washed 3 times with NMP and 3 times with DCM and then dried. 1 mL of a 50% TFA solution in DCM was added to the reaction vessel and mixed for 10 min. which cleaves the Boc-protecting groups. The reaction product was drained, and the deprotection step was repeated. The resin reaction product was washed 3 times with DCM and neutralized with a 2% solution of NEt$_3$ in DCM; after standing for 5 minutes, washing and neutralization was repeated. The resulting resin product was washed with NMP 3 times and split into two equal portions. To the first resin portion, the coupling procedure was repeated, as depicted in the left-hand portion of FIG. 16, with thymine precursor from Example 5 (for TT dimer). The second resin portion was coupled using adenine precursor from Example 11, as depicted on the right-hand side (to create a TA dimer). The two separate reaction mixtures were each washed 3 times with NMP, and 3 times with DCM. Following drying, each resin was treated with 1.5 mL of a 2% hydrazine solution in MeOH for 1 hour, and each solution was collected. Each cleavage process was repeated and combined with the previous organic solutions. After drying, the left-hand dimer shown was obtained from the first reaction vessel, and the right-hand dimer shown was obtained from the second reaction vessel. Both dimers were isolated as single products in greater than 95% yield. Both dimers include the C-terminal linker discussed hereinbefore.

EXAMPLE 26

Figure 17:
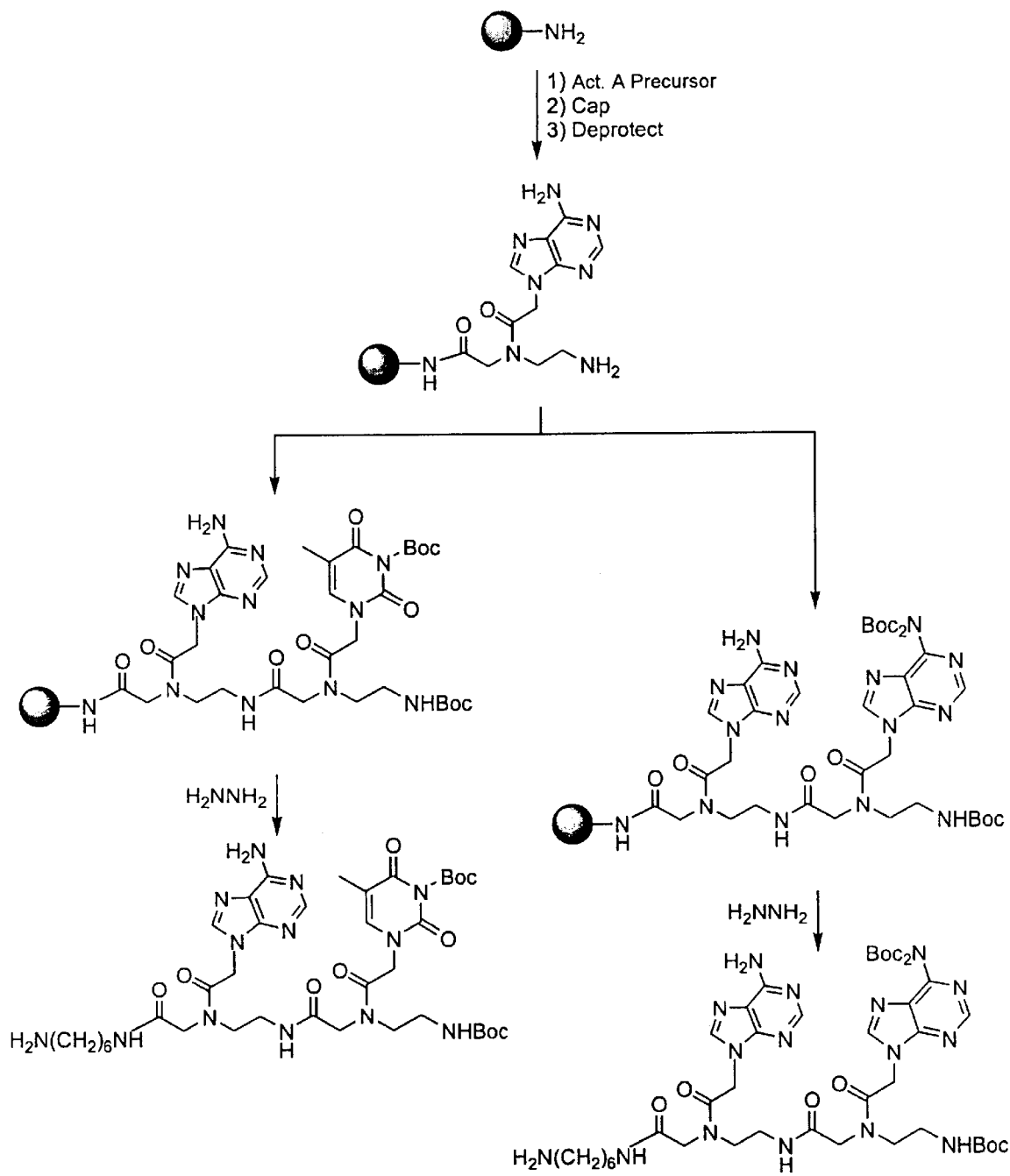
FIG. 17 is a schematic similar to FIG. 16 where the reaction begins with a step which results in an adenine PNA monomer being coupled to the resin.

Solid phase syntheses of other PNA dimers are depicted in FIG. 17.

40 mg of CLEAR-DDE-hexamethylene diamine resin was placed in 2 mL reaction vessel and preswelled with 1 mL NMP for 20 min, then the solution was drained. A stock 0.2 M solution of tris-Boc-protected adenine precursor of Example 11 was prepared in anhydrous NMP, and 3 equivalents of the precursor were added to the swollen resin as in Example 22. The reaction mixture was left to stir at room temperature for 1 hour and then drained. The resin reaction product was washed 3 times with NMP and then treated with a capping solution of 1 M NEt$_3$ and 0.5 M acetic anhydride in NMP (500 μL) for 5 minutes before draining. The resin product was washed 3 times with NMP and 3 times with DCM and then dried. 1 mL of a 50% TFA solution in DCM was added to the reaction vessel and mixed for 10 min. to cleave the Boc-protecting group at the N-terminus, with the other Boc-protecting groups also being cleaved. The resin reaction product was drained, and the deprotection step was repeated. The resin product was washed 3 times with DCM and neutralized with a 2% solution of NEt$_3$ in DCM; (after standing for 5 minutes, washing and deprotection were repeated). The resulting resin reaction product, shown in FIG. 17, was washed with NMP 3 times and split into two equal portions. To the first resin portion, the coupling procedure was repeated with the thymine precursor of Example 5 as shown on the left-hand side (to create the AT dimer). The second resin portion was coupled using the adenine precursor of Example 11 (to create the AA dimer). The two separate resin reaction products were each washed 3 times with NMP and 3 times with DCM. Following drying, each material was treated with 1.5 mL of a 2% hydrazine solution in MeOH for 1 hour, and the solutions collected. This cleavage process was repeated, and each set of combined organic solutions was dried, affording the left-hand AT dimer from the first reaction vessel and the AA dimer from the second reaction vessel. Both dimers were isolated as single products in greater than 95% yield.

EXAMPLE 27

Figure 18:
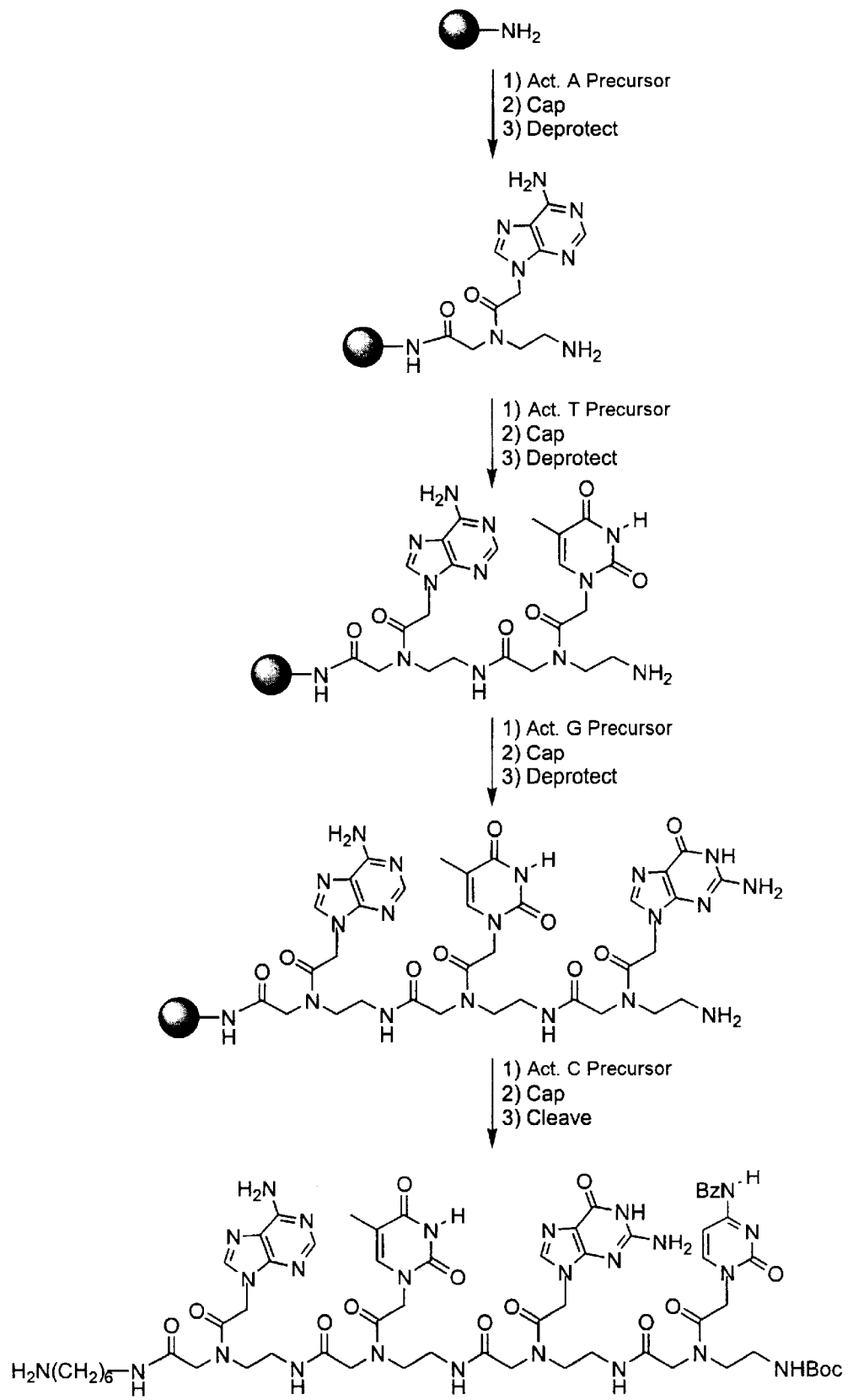
FIG. 18 is a schematic showing a synthesis of a PNA tetramer employing the strategy depicted in FIGS. 16 and 17.

Solid phase synthesis of a PNA tetramer as depicted in FIG. 18.

The steps of Example 26 were repeated using only 20 mg of CLEAR-DDE-hexamethylene diamine resin and following the strategy depicted in the left-hand series of schematics to create the AT dimer attached to the resin. The resin was treated with a capping solution of 1 M $NEt_3$ and 0.5 M Acetic anhydride in NMP (500 $\mu$L) for 10 minutes and drained. The resin reaction product was washed 3 times with NMP and 3 times with DCM and then dried. 1 mL of a 50% TFA solution in DCM was added to the reaction vessel and mixed for 10 min. to remove the protecting groups. The reaction mixture was drained, and the deprotection step was repeated. The resin was washed 3 times with DCM and neutralized with a 2% solution of $NEt_3$ in DCM obtaining the illustrated dimer. The resulting resin product was washed 3 times with NMP, and the earlier coupling procedure was repeated, this time using the bis-Boc-protected guanine precursor of Example 13 to afford a resin-trimer reaction product which is shown following deprotection to ready it for the next coupling step. A final coupling cycle utilized the Boc-protected cytosine precursor of Example 9. The resin reaction product was washed 3 times with NMP and 3 times with DCM. The dried material was treated with 1.5 mL of a 2% hydrazine solution in MeOH for 1 hour, and the solution collected. This cleavage process was repeated, and the combined organic solutions were dried to afford the tetramer shown, including the desired linker, as an alkyl amide at the C-terminus.

A Convergent Approach to PNA Oligomer Synthesis

For many years organic chemists have employed a convergent approach to large molecule syntheses because it reduces the number of linear steps needed to arrive at the final product and it can significantly improve the yield. To date, most chemists working on the syntheses of PNA or related compounds have approached these syntheses as linear process. One reason for this has been the ease with which a linear sequence can be prepared relative to the extreme difficulty involved in the preparation of short PNA oligomers with a free carboxy terminus suitable for coupling. However, such free carboxy terminus PNA oligomers can now be prepared, in either solution or solid-phase, with the appropriate selection of protecting groups as long as the terminal carboxy group can be suitably protected to prevent unwanted piperazinone formation from occurring. One such solid-phase approach to the preparation of free carboxy terminus PNA dimer is hereinafter described, along with the coupling of this product to a resin-bound PNA dimer to form a tetramer. This process can similarly be utilized for the formation of trimers and tetramers with free carboxy termini. The coupling reaction can likewise be used to couple dimer to dimer, dimer to trimer, trimer to tetramer, etc., thereby forming PNA oligomers of desired length in a convergent manner.

EXAMPLE 28

Figure 19:
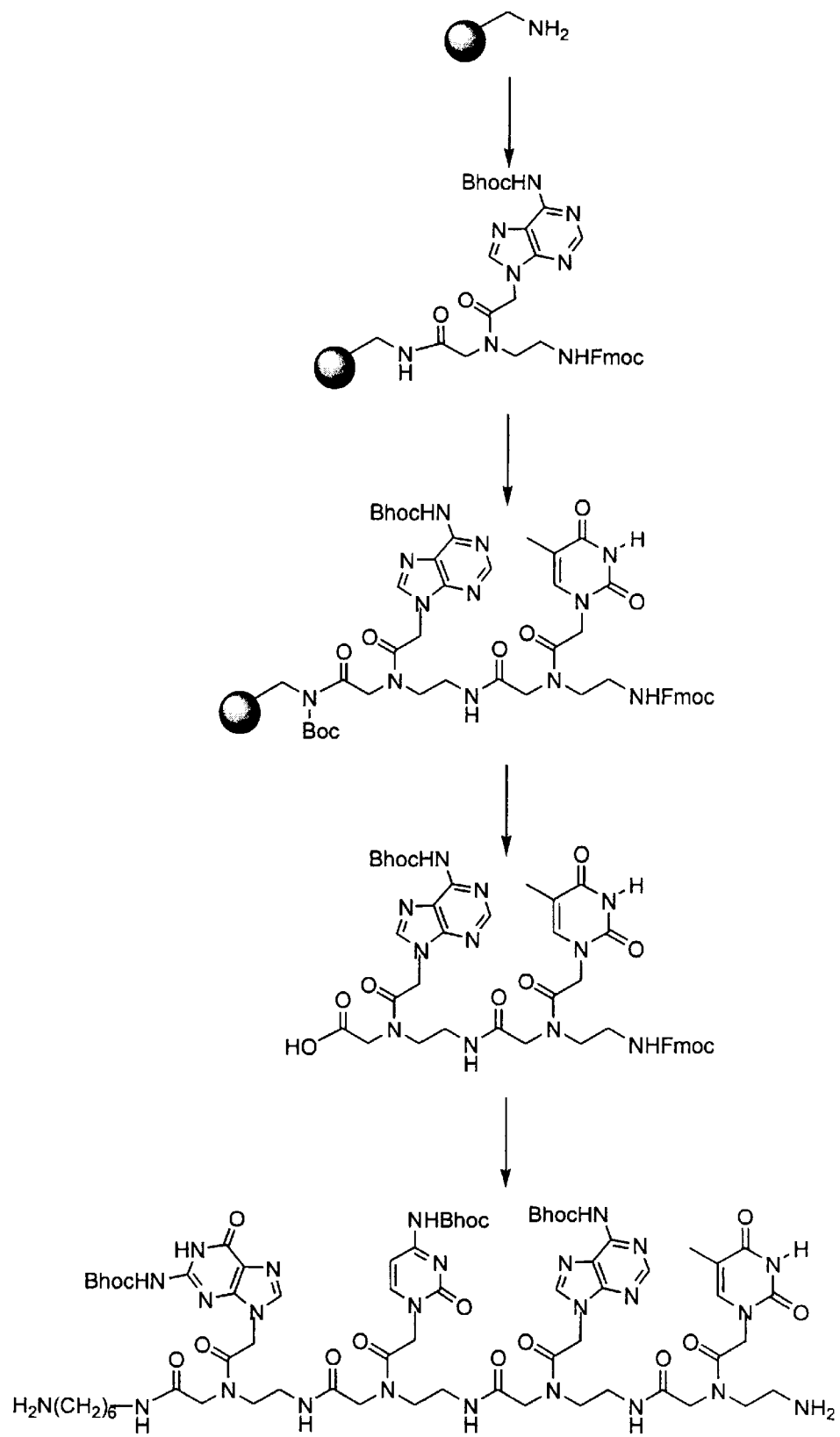
FIG. 19 is a schematic illustrating an alternative convergent synthesis to that depicted in FIG. 18.

Preparation of a PNA dimer carboxylic acid is first effected as depicted in FIG. 19.

40 mg of aminomethyl polystyrene resin was placed in 2 mL reaction vessel and preswelled with 1 mL NMP for 20 min, then the solution was drained. A standard Fmoc-PNA synthesis protocol as well known in this art was used to couple an adenine PNA monomer to this resin with the adenine primary amino group protected by benzhydryloxy-carbonyl (Bhoc) groups. The resin reaction product was washed 3 times with NMP and 3 times with DCM and then dried. Ten equivalents of $Boc_2O$ and 5 equivalents on DMAP in DMF were added, and mixing was performed for 4 hours to add a Boc-protecting group to the amido moiety in the resin linker. The resin reaction product was first washed with a dilute solution of aqueous HCl in THF and then was washed 3 times with NMP. A 20% solution of piperidine in DMF was added to remove the Fmoc-protecting group, and mixing followed for ten minutes. Then, the washing and deprotection process was repeated. Next, the resin product was washed 3 times with NMP, and a coupling reaction was carried out with an Fmoc-protected thymine PNA monomer. The resulting resin reaction product was washed 3 times with NMP, and 3 times with THF. After drying, the dried resin reaction product was treated with a 6:1 mixture of THF and 1N LiOH. After one hour, the reaction mixture is concentrated to $\frac{1}{6}^{th}$ of its original volume and then acidified to pH 4 with a 1N solution of HCl to cleave the AT dimer from the resin. Precipitation with ether affords the free acid AT dimer shown, in 90% yield, which is thereafter coupled to a resin-bound dimer.

A resin-bound GC dimer is prepared by a PNA synthesis protocol as generally described in Examples 25 and 26 using CLEAR-DDE-hexamethylene diamine resin. Three equivalents of the free acid AT dimer were pre-activated by stirring with 0.98 equivalents of HATU and $NEt_3$ for 1 minute and then added to the resin-bound dimer containing a terminal free amine. The reaction was stirred for 90 minutes and then drained. The resin reaction product was washed 3 times with NMP, 3 times with MeOH and 3 times with DCM. Cleavage with $NH_2NH_2$ gave the desired tetramer having the desired C-terminal linker.

A universal PNA library as contemplated herein may be constructed with any length of PNAs, for example, from tetramers to dodecamers; however, the longer the sequence of the PNAS, the higher the specificity toward the complementary DNA or RNA gene fragments. Unfortunately, the synthesis of a library of PNA sequences of more than about 8 bases is not economically feasible, due to the large number of compounds that would need to be synthesized. For example, a dodecamer universal PNA library requires synthesis more than 16 million ($4^{12}$) discrete compounds. Although an octameric library of PNAs may be synthesized using standard solid-phase coupling and protection/deprotection reactions, even an octameric library requires synthesis of numerous individual species, more than 65,000. Thus, in one preferred embodiment, one or more universal nucleotide bases are incorporated into such a library, essentially as placeholders, thereby extending the library's usefulness without requiring synthesis of additional species. For example, in a most preferred embodiment of such a library, the sequencing capability of an octameric universal library is obtained through the synthesis of only about 256 individual compounds. This is accomplished by incorporating a universal nucleotide base at every other nucleotide position in the octamer and is further made expedient by employing the novel syntheses described hereinbefore.

Figure 20:
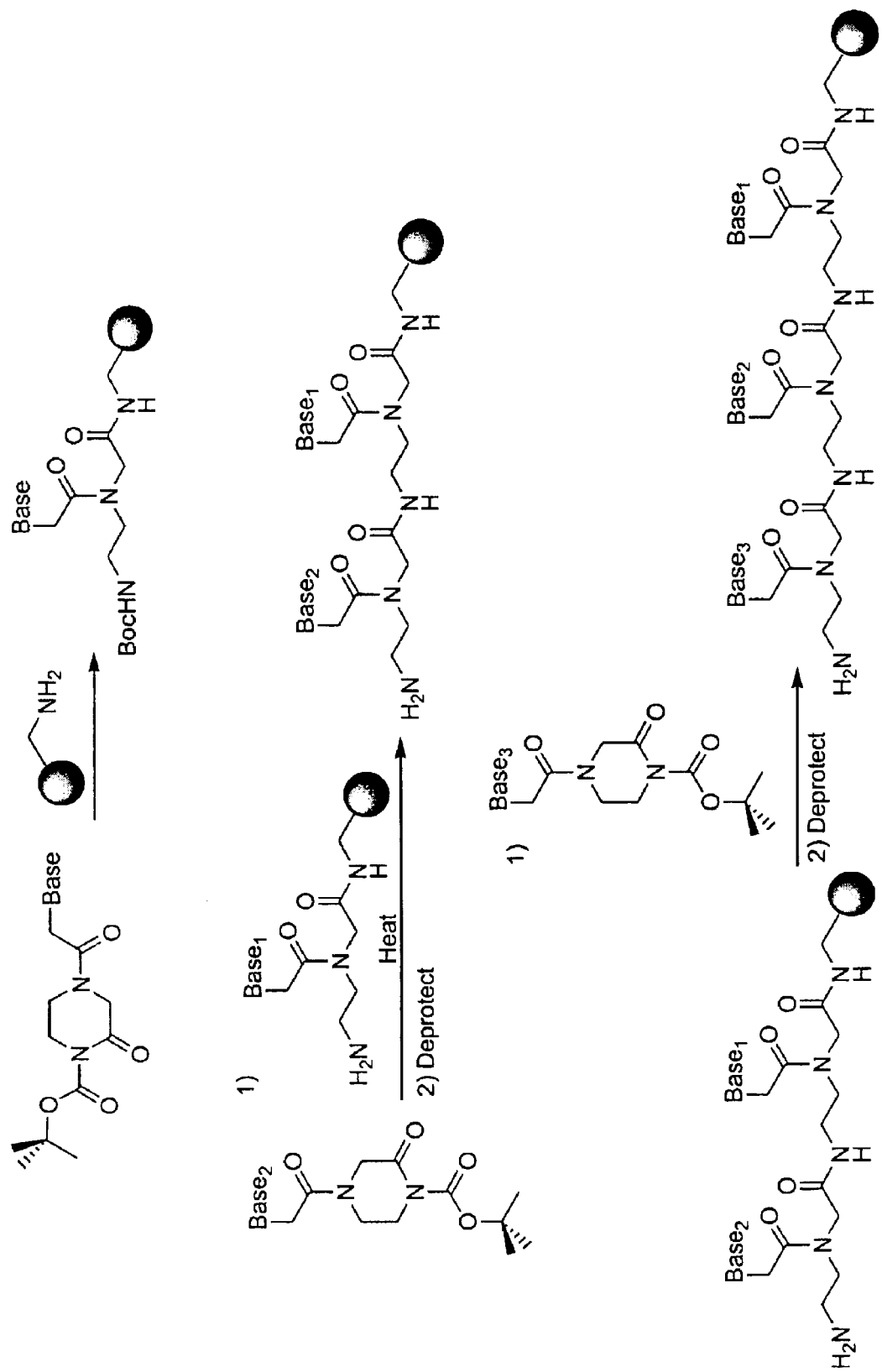
FIG. 20 is a schematic of the synthesis of a resin-bound PNA trimer.
Figure 21:
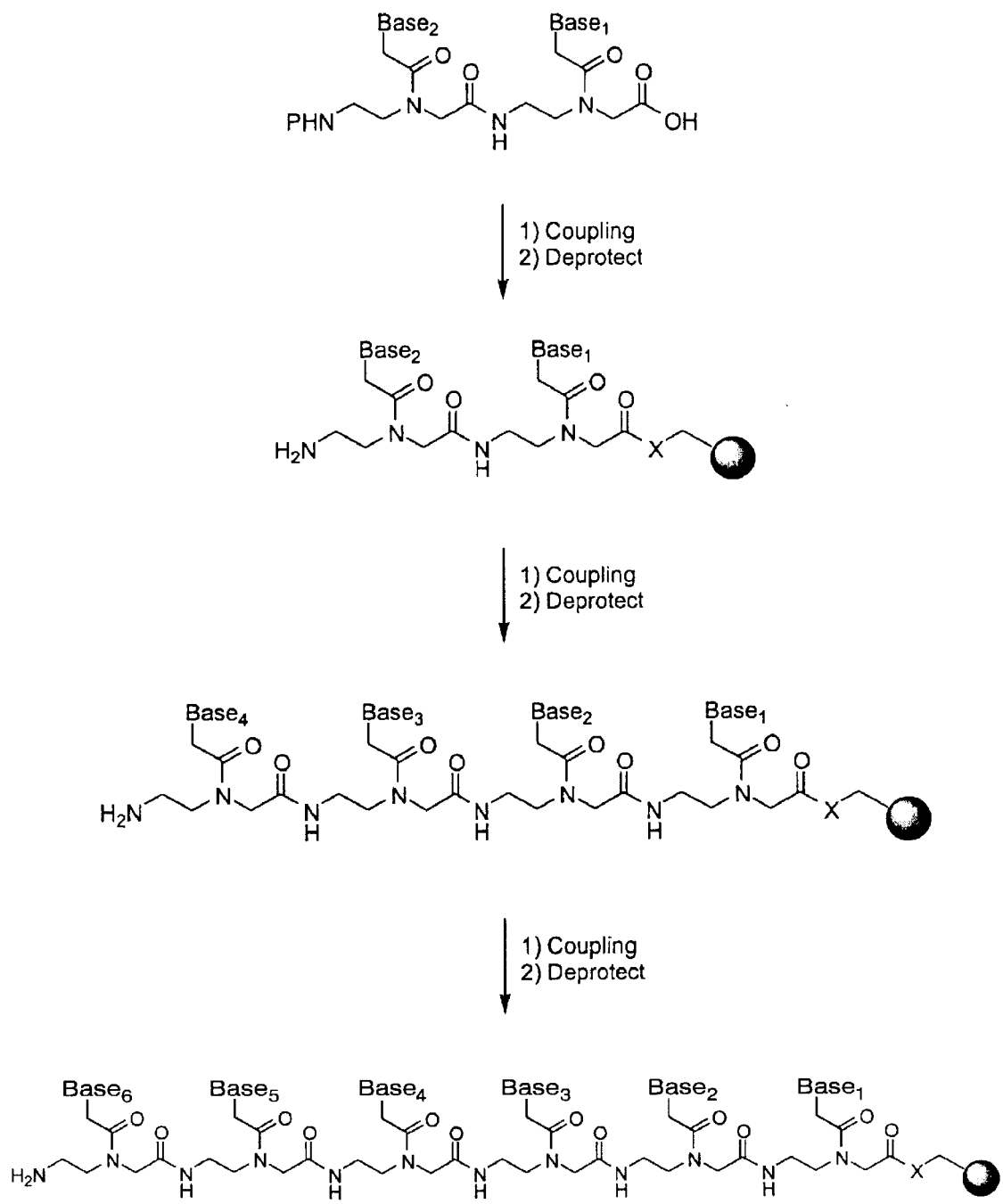
FIG. 21 is a schematic of an improved method of synthesis of a hexameric PNA oligomer.
Figure 22:
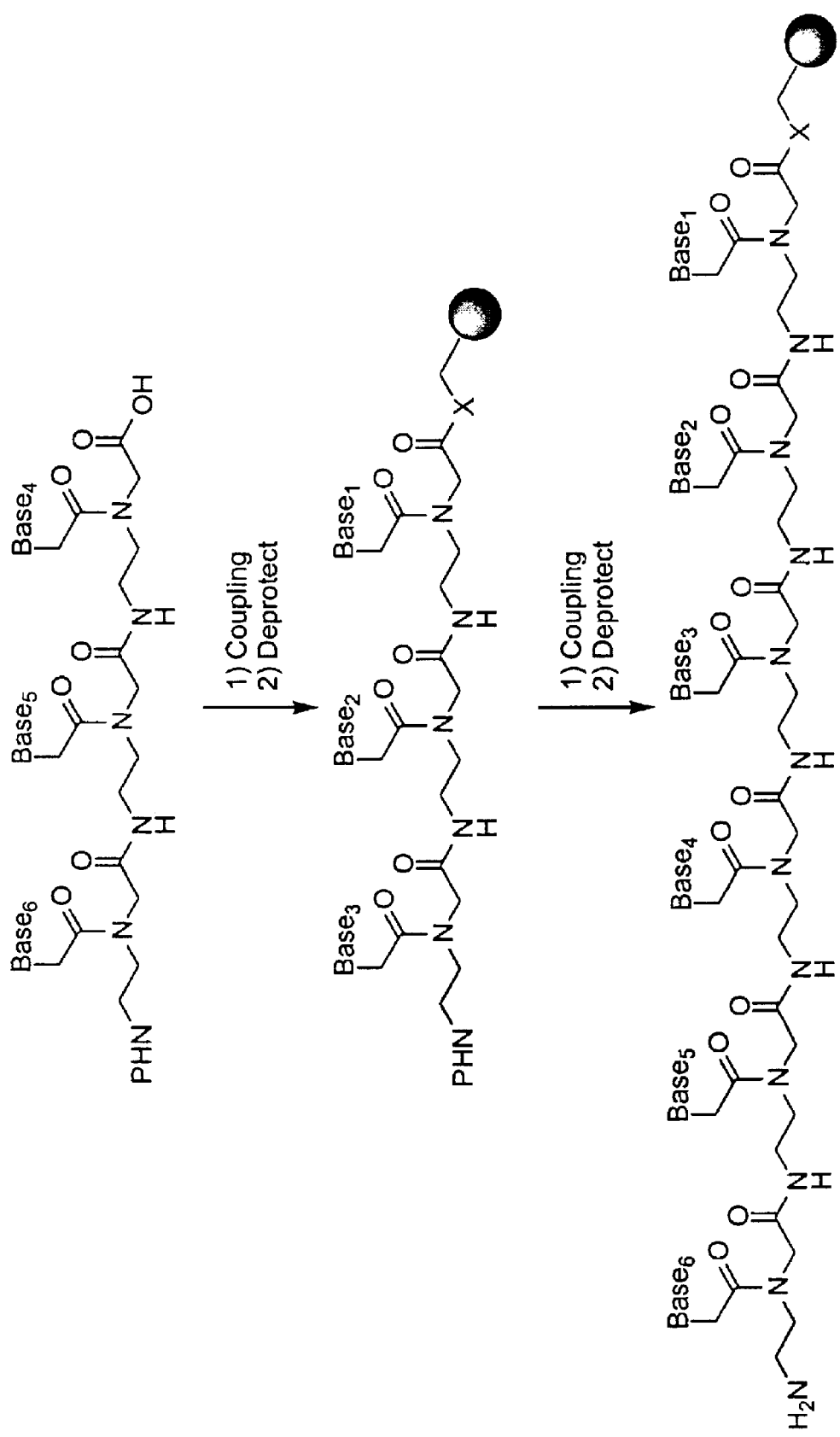
FIG. 22 is a schematic of an alternative improved method of synthesis of a hexameric PNA oligomer.

FIG. 20 shows a general scheme for the synthesis of a PNA trimer which can be continued to create oligomers of greater lengths. A suitably protected preactivated PNA precursor is used to couple a first PNA monomer to a resin or other nucleophile, followed by deprotection to ready it for the second step. Addition of a second PNA monomer using a suitable activated precursor and then its subsequent deprotection following coupling gives the deprotected dimer attached to the resin. Repetition of this cycle continues until the desired chain length of PNA is reached, for example, a PNA trimer, as illustrated in FIG. 20. FIGS. 21 and 22 illustrate the conventional convergent syntheses of PNA oligomers. In such an approach, a library of suitably protected PNA dimers or trimers are used as the starting material for the syntheses. A PNA dimer is first coupled to a resin and deprotected in FIG. 21. A second dimer is added by repeating the cycle to result in formation of a tetramer. The process is repeated again, and in three coupling cycles, a hexamer is prepared. This process reduces the number of coupling steps and the production of side products, and assuming a finite number of the desired dimers can be earlier prepared and then used as stock items, it can be economical from this standpoint. Alternatively, as shown in FIG. 22, suitably protected trimers can be used in such convergent synthesis approach to achieve formation of a PNA hexamer in only two coupling steps. As mentioned, inventories of both trimers and dimers may be used in certain convergent syntheses to prepare PNAs of particular lengths, for example, pentamers, heptamers, and undecamers.

Figure 23:
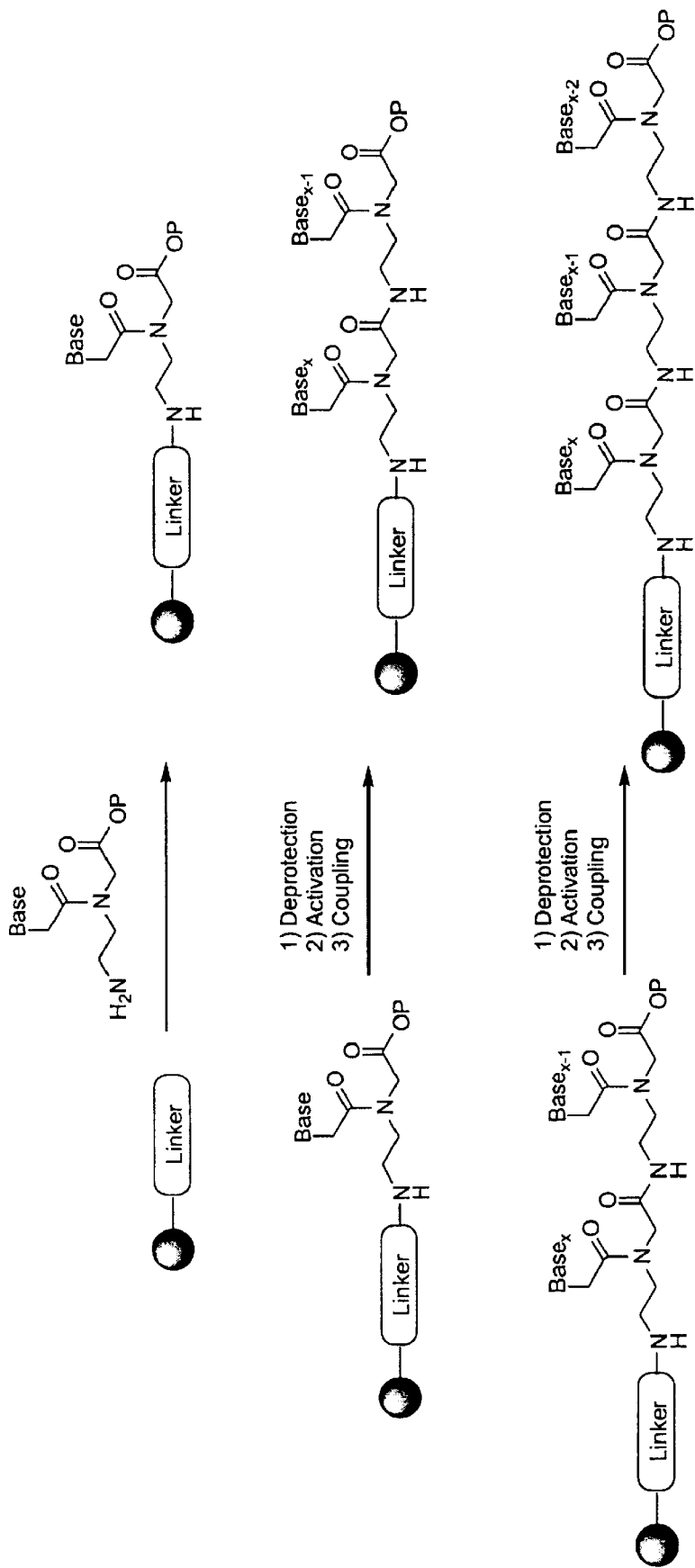
FIG. 23 is a schematic showing the inverse synthesis of a PNA molecule.

The inverse synthesis of a PNA molecule is shown in FIG. 23. A suitably protected monomer is coupled to a resin through its α-amino group via an appropriate linker with its carboxy terminus protected. Deprotection of the terminal acid, followed by activation permits addition of a second monomer again having its carboxy terminus protected. The coupling cycle is then repeated to give the trimer, and through continued cycling, the desired PNA chain length is obtained. Activation of the acid on the resin may simplify recovery of the PNA monomer and reduce the overall cost of synthesis.

While the syntheses just described involve solid-phase synthesis, those of skill in the art will appreciate that solution-phase synthesis of PNAs may likewise be accomplished by simply replacing the resin with a suitable protecting group for the particular terminus.

Synthesis of Universal PNA Libraries
A. Use of Universal Nucleotide Bases

In a preferred embodiment contemplated herein, universal nucleotide bases, such as inosine, nitropyrole and/or 5-nitroindole, which are capable of binding to any of the four nucleotide bases, are incorporated into the universal library in specific, carefully chosen positions within each oligomer. Such universal-base-containing libraries require the synthesis of fewer individual PNA species, but have a comparable scope and function of their larger-sized counterparts. For example, in a most preferred embodiment, a universal library is prepared having at least four base positions and at least half the total number of base positions occupied by a conventional nucleotide base (A, C, T or G), with the remaining base positions being filled by a selected universal base.

Thus, for example, by substituting the conventional nucleotide bases located in just two positions in a nanomeric library—such as the third and seventh positions—with universal nucleotide bases, a universal library of only 16,384 ($4^7$) different PNA species need be synthesized. This library of "pseudo-heptamers" possesses comparable scope and function to the 262,144 species conventional nanomeric PNA library, yet is considerably more cost effective to prepare than its nanomeric counterpart.

In another embodiment, substitution of conventional nucleotide bases with universal bases may be expanded to involve every other nucleotide base position within the PNA. In this manner "mini-libraries" of particularly small size may be quickly, easily and inexpensively prepared, further enhancing the flexibility of universal libraries. For example, in a most preferred embodiment, an octameric library having only four conventional nucleotide bases and four universal nucleotide bases is prepared. Such a universal library requires synthesis of only 256 different PNA sequences as opposed to the 65,536 PNA sequences required for a wholly conventional octameric PNA library. Again, the hybridization capacity of such a library is similar to that of the conventional counterpart. Further, the stability of the individual PNA species is greater in an octamer than in a tetramer. Thus, use of the universal octameric library containing universal nucleotide bases should provide significantly better results than use of a universal tetrameric library containing only conventional nucleotide bases.

While it is expected that increased substitution of conventional bases with universal nucleotide bases in a PNA library will reduce the usefulness of the library for certain purposes, such universal-base-containing libraries provide a fast, accurate, inexpensive tool for initial screenings of compounds. As will be discussed further below, the data and information collected from the screenings of such libraries may be used to determine the optimum sequence base identity of PNA oligomers for further screening and testing.

B. Apparatus for Library Synthesis—Hydrogel

Relatively large PNA libraries, according to the present invention, can be constructed using any one of a number of apparatus, including standard multiwell plates, microchips or spot membranes. For example, octameric DNA chips have been constructed by light-directed, spatially addressable chemical synthesis (Fodor, et al. *Nature* 364:555 (1993)). This approach makes use of a parallel process in which sites on a silica chip are illuminated through the apertures of a photolithographic mask, with resulting activation for chemical coupling with protected DNAS. Protection groups are removed from terminal DNAs with illumination at each subsequent step, resulting in the activation of another set of sites for linkage with a new set of protected DNAs, i.e., preferably the dimer or trimer selected for addition to the growing DNA. With this approach, DNAs are built up on the silica chip, with the location and composition of sites dependent on the pattern of illumination and the order of chemical coupling reagents used. The result is a high-density array in which the sequence of the DNA at each site is known. The binding of fluorescence-labeled DNA or RNA fragments to specific sites can be detected by fluorescence microscopy. This permits, for example, the identification of the DNA or RNA fragments based on the complementary DNA or PNA sequences to which they bind.

Although such a light-directed, spatially addressable chemical synthesis method may be employed, as well as various other apparatus and methods in the production of a PNA library according to the present invention, an improved method of library synthesis is presented herein. In this preferred embodiment, the PNAs are conjugated to a linker molecule having a free amine at the non-conjugated end. Using this amine, the PNAs are bound to a pre-hydrogel (such as Hypol, manufactured by Hampshire Chemical Corporation) having active isocyanate functionalities. In contrast to DNA-based oligonucleotides, PNAs are soluble in organic solvent and thus may be coupled to the pre-hydrogel using such organic solvents. The resulting PNA-hydrogel solution can be treated with a solution of water and water-miscible organic solvent, such as acetone. When the free isocynates react with water, the PNA-bound pre-hydrogel crosslinks and liberates $CO_2$. The addition of water-miscible organic solvent during the crosslinking process is used to control the amount and speed of $CO_2$ generation so that the resulting hydrogel remains transparent.

Most preferably, the universal PNA library according to the present invention is not randomly synthesized but is methodically synthesized. Methodic synthesis, as used herein, refers to synthesis of the library in such a manner that the location and sequence base identity of the individual species of the library are known, so that positive screening results do not require sequencing of the PNA oligomer. Thus, while the library synthesis may be and preferably is automatically performed, each species of the library is synthesized in a separate vessel, such as in separate microliter wells.

Once the PNA library, or the individual PNA oligomers to be tested, if less than the complete library, is isolated on the transparent hydrogel, screening the library with labeled DNA or RNA fragments is greatly facilitated. Thus, for example, the solvents are removed from the PNA-hydrogel membrane and the membrane is treated with the fluorescence-, radioisotope-, metal or otherwise-labeled DNA or RNA fragments in an aqueous medium. After washing the swollen hydrogel thoroughly to remove any unspecifically bound DNA or RNA fragments, the binding of labeled DNA or RNA fragments to specific sites can be monitored. To accelerate the washing procedure, electric fields can be applied with microelectrodes.

This process of creating a universal PNA library bound to a hydrogel membrane and then screening labeled compounds therewith, is simpler and less expensive than the microchip method and thus is preferable to that and other methods. Furthermore, the amount of PNA bound to the hydrogel can easily be controlled to provide a high density of PNAs; thus, a higher amount of labeled DNA or RNA fragments, can be captured, thereby increasing the sensitivity of the assay. PNA-hydrogel formulations can be bound to microwell plates, or spotted onto membranes made of fabrics like nylon or similar polymers. Most preferably, whichever support is chosen, it will be transparent so that a multi-spot array assay, as described below, may easily be performed.

C. Immobilization of PNAs on Membrane Arrays

An alternative immobilization method, that is particularly useful for the rapid evaluation of DNA polymorphisms, is provided by screening PNA oligomers isolated on membrane arrays as described, for example, by Weiler J. et al., *Nuc Acid Res* 25:2792, 1997. This method allows a large number of DNA samples to be quickly assayed. For example, arrays of up to 1,000 different PNA oligomers can be synthesized on a polymer membrane using a robotic device, such as the one developed by Frank, R. for parallel oligopeptide synthesis (Tetrahedron 48:9217, 1992). By using different enzymatically cleavable linkers to attach the PNAs to the membrane, individual PNA sequences can be selectively removed from the solid support for further analysis.

1. Attachment of Linkers to a Membrane Array

The attachment of linkers to an amino-functionalized membrane was accomplished by derivatizing the membrane with a peptide spacer, i.e. glutamic acid-(-tert-butylester)-(ε-aminohexanoic acid)-(ε-aminohexanoic acid) using standard Fmoc-chemistry. The respective amino acid derivative was activated by the addition of 1.2 equivalents diisopropylcarbodiimide (DIC) and 1 equivalent HOAt and used at a final concentration of 0.2 M in N-methyl-2-pyrrolidone (NMP). The membrane was submerged in this solution for 15 min., washed with dimethylformamide (DMF), and the Fmoc-groups were removed by a 5 min incubation in 20% piperidine in DMF. The membrane was again washed in DMF, rinsed with ethanol and dried. Following addition of the spacer, the membrane was mounted in an Automated SPOT ROBOT (Frank, R. *Tetrahedron* 48:9217, 1992) and a grid of the desired format was spotted using, at each position, 0.3 μL of activated Fmoc-lysine-(ε-tert-butyloxycarbonyl). After a reaction time of 30 min, the membranes were treated with 5% acetic anhydride in dry NMP to cap all amino groups outside the spotted areas. The membrane was then washed and deprotected, and the spots were visualized with a solution of 0.01% bromophenol blue in DMF (Krchnak V. et al. *Int. J. Pep. Protein Res.*, 32:415, 1988).

2. Conjugation of PNAs to the Membrane Array

PNA capture sequences were deposited to the individual spots on the membrane array using the ASP 222 Automated SPOT Robot. The complete synthesis cycle comprised: coupling (spotting of activated derivative followed by 20 min reaction time after placing material to the last spot); 5 min of acetylation in 5% acetic anhydride in DMF; five washes of 1 min each in 10 mL DMF; 5 min of deprotection with 20% piperidine in DMF; staining with 0.01% bromophenol blue in DMF; three rinses in 10 mL ethanol and subsequent drying. After completion of the synthesis, the PNA oligomers were deprotected by a 1 h incubation in a mixture of 90% trifluoroacetic acid, 5% water and 5% triethylsilane. Once immobilized on the array, the PNAs are ready for the high throughput screening process.

Improved High Throughout Screening Assays

Having once synthesized the universal PNA library, the focus is upon screening the library for those PNA oligomers capable of binding to the target nucleotide molecule(s). In one aspect, the following assays directed to the selection of biologically active sequences as potential diagnostic and/or therapeutic candidates may be employed. Additionally, assays that permit the structural and/or functional identification of newly discovered genes using PNA probes from the universal library, according to the prior art according to the prior art may be employed. Finally, assays may be employed that allow the identification of genomic mutations, such as single nucleotide polymorphisms, in either genomic DNA or PCR-amplified DNA for genetic diagnosis of disease states as well as the rapid screening of at-risk populations. Such screenings will be particularly useful for genetic counseling.

The assays described herein may be performed by hybridizing the PNAs to DNA fragments which are bound to solid supports or, alternatively, by immobilizing the PNAs and using them as DNA-capture agents to capture the test DNA sequence. Any of a number of methods of detecting PNA hybridization to the test DNA or RNA fragment.

A. DNA Hybridization with PNA Probes

1. Hybridization without Signal Amplification

One method contemplated herein for the screening of the PNA library, is hybridization of PNA probes to the DNA of interest without signal amplification. This method is particularly suited for the functional characterization of a newly discovered gene. The gene sequences of interest are immobilized on a solid support such as multi-well microplates or nylon membranes. Hybridization reactions are preferably performed in 10 mM sodium phosphate buffer, or equivalent, at pH 7.4 and at about 80°, thereby taking advantage of the ability of PNAs to hybridize to their complementary DNA sequences under low salt and high temperature conditions. Non-specific binding sites are preferably blocked with a 1 mg/mL solution of bovine serum albumin (BSA), or a 0.1% SDS solution in 10 mM sodium phosphate buffer at pH 7.4 and washed thoroughly. The PNA probes are preferably labeled, such as with a radioactive isotope or biotin, prior to hybridization. Following hybridization of the labeled probe to the support-bound DNA, the label is activated. If the label is a radioisotope, of course, no activation is required. In the case of a biotin-labeled PNA probe, specific signal can be detected by reading biotin with avidin labeled with fluorescence emitters. Methods of fluorescence detection are well known to those of skill in the art. In general, the wavelength chosen to be measured by the fluorescence reader will be that corresponding to the particular type of fluorescence used to label the biotin, e.g., fluorescine, rhodamine, etc.

2. Hybridization with Signal Amplification

In some cases, for example, where the DNA sample of interest is only available in small quantities or where only a small portion of a lengthy strand of DNA is of interest, specific signal amplification may be required to enhance the signal-to-noise ratio and further increase the sensitivity of the assay. This is particularly relevant where PCR amplification of DNA is either not possible or not desirable. In a preferred method of signal amplification, the PNA probe is conjugated with a recognition tag which is then recognized by a second specific probe linked to biotin. This complex can then be detected with fluorescence-labeled avidin as previously described. The signal can be further amplified by adding multiple recognition steps similar to the multi-recognition steps currently used in multi-layer sandwich enzyme-linked immunoassays. As outlined above, hybridization most preferably takes place in 10 mM sodium phosphate buffer, at pH 7.4 and at about 80°. Following hybridization, the system is cooled to 37° for signal amplification.

Examples of recognition tags useful for the signal amplification process as contemplated herein, include but are not limited to, bifunctional derivatives of macrocyclic tetraza-cyclododecane chelates of the basic 13(ane)N4 formula, such as nitro-benzyl-DOTA (see, for example, Moi M. K. et al., *J. Am. Chem. Soc.* 110:6266, 1988; Renn O. and Meares C. F., *Bioconj. Chem.* 3:563, 1992; and U.S. Pat. No. 4,678,667, 1987). Bifunctional DOTA derivatives contain four NH groups in a 12-atom ring configuration. The N-bound hydrogens are amenable to substitution with functional groups such as —$CH_2$—COOH or —$CH_2$—$COOCH_3$; the nitrogens and the substituted carboxyl groups form coordination bonds with rare earth metal ions, including non-radioactive lanthanides like indium, gallium or lutetium, resulting in tight metal complexation.

A number of other bifunctional macrocyclic chelates may also be used herein, including PA-DOTA (alpha-[2-(4-aminophenyl)ethyl]-1,4,7,10-tetraazo-cyclodo decane-1,4,7,10-tetraacetic acid), and PA-DOTMA (alpha-[2-(4-aminophenyl)ethyl]-1,4,7,10-tetraazo-cyclod odecane-1-acetic-4,7,10-tri(methylacetic) acid), as disclosed in U.S. Pat. No. 5,435,990 incorporated herein by reference, in its entirety. Still other bifunctional macrocyclic chelates of the basic 13(ane)N4 formula include TRITA, TETA and HETA (see, U.S. Pat. No. 4,678,667, also incorporated herein in its entirety.) Additionally, linear chelates such as EDTA or DTPA may be used.

Another example of recognition tags that can be linked to PNA probes and used according to the present invention are DNA sequences capable of hybridizing specifically with a second set of DNA or PNA probes which are themselves conjugated to the bifunctional macrocyclic chelates as described above. Such recognition tags must be carefully designed to prevent non-specific PNA-DNA hybridization with surface-bound DNA, which will mask the specific PNA-DNA hybridization and therefore interfere with the specificity of the assay. An example of a suitable probe as contemplated herein, is a bacteriophage lambda-specific sequence. DNA-bound PNAs containing such specific recognition tags can then be detected using the signal amplification systems described below.

The chelate recognition tags are preferably linked to each PNA or (DNA) probe via a space linker comprising, for example, an aliphatic chain containing 3 to 6 carbon atoms, to prevent the chelate from causing interference with the binding of the PNA probe to its complementary DNA sequence, such as by sterically hindering such binding. The DNA-bound PNA probe conjugated with the chelate recognition tag can be, and preferably is, detected using a specific anti-chelate monoclonal antibody (MoAb), such as a MoAb recognizing non-radioactive indium-labeled DOTA. The antibody is conjugated with biotin, and the DNA-bound PNA is then detected with fluorescence-labeled avidin.

Further signal amplification can be achieved by reacting the DOTA-conjugated PNA probe with a murine anti-DOTA MoAb. Such antibody can be probed with a second antibody, such as a goat anti-mouse antibody, which in turn can be probed with a third antibody, such as a sheep anti-goat antibody, which in turn can be probed with a fourth antibody, such as horse anti-sheep, and so forth. The last antibody probe, is biotin-conjugated prior to its addition to the reaction vessel and, following, its hybridization to the previous antibody, it is reacted with fluorescine-labeled avidin and the resulting signal is detected as previously described.

In addition to using monoclonal antibodies to amplify the assay's signal, one of the antibodies, such as the horse-antisheep antibody outlined on the scheme above, can be probed with an antibody, such as a dog anti-horse, having a branched dextran of MW about 40,000 conjugated thereto. This is then probed with an anti-dextran antibody which is conjugated to a branched, water-soluble polymer, such as polyvinyl alcohol or polyvinyl pyrrolidone, which polymer is further conjugated to biotin. The biotin is then reacted with fluorescence-labeled avidin as previously described and the significantly amplified signal is detected as above.

Advantageously, the method of screening DNA fragments with PNA probes conjugated to a recognition tag can be modified to permit the consecutive detection of multiple DNA sequences in the same well. In this modified method different PNA probes are labeled with different chelates which can then be recognized by their corresponding MoAbs. Each antibody is then probed with avidin conjugated to a different fluorescence-emitters. In this way each probe may be separately detected by the characteristic wavelength of light it emits.

B. Alternative Detection Methods Using PNA Probes

One alternative detection system contemplated herein, is the use of luminescence rather than fluorescence. According to this method, the antibody used in the final recognition step is conjugated with an enzyme such as alkaline phosphatase instead of biotin. The signal is then developed by addition of a luminescent phosphatase substrate and detected using a standard luminometer.

Another alternative detection system contemplated herein is based upon detection of the kinetics of association ($K_a$) or dissociation ($K_d$) of the DNA-PNA hybrid using, for example, a BIAcore (Biomolecular Interaction Analysis) surface-plasmon resonance detection apparatus (Pharmacia, Uppsala). According to this method, a gold-covered sensor chip within the detection apparatus is treated with a layer of dextran linked to avidin. A PNA probe, conjugated via a linker to biotin, is immobilized on the avidin-dextran coated surface and captures complementary DNA sequences. The signal measured by the apparatus is proportional to the change of the refractive index at the surface of the chip and is generally assumed to be proportional to the mass of the substance bound to the chip (Jonsson 1991; Karlsson 1993). By measuring the amount of bound substance as a function of time, when a solution containing the complementary strand passes over the chip, the kinetics of association of the DNA to the immobilized PNA probe can be determined. This system functions only in a single read-out mode, and thus, may not be suitable for analysis of large samples. However, it may be suitable when detailed kinetic determinations of specific PNA-DNA interactions are desired or required.

C. Polymorphism Detection Using PNA Probes

In a modified detection assay, contemplated herein, PNAs having sequences complementary to conserved sequences adjacent to areas of DNA containing single nucleotide polymorphisms or other areas of interest are immobilized on a solids support. The immobilized PNAs are then exposed to the DNA fragments of interest and specific PNA-DNA hybridization is allowed to occur. After removing any non-hybridized DNA, the PNA-bound DNA is detected using one of the above-described methods. By selectively capturing only DNA fragments containing the mutation of interest, this modified assay permits concentration of the DNA sample, further increasing the signal to noise ratio.

D. Biological Activity Assay

The biological activity of selected PNAs may initially be assessed in cell free systems by various methods. For example, direct inhibition of protein synthesis may be tested using cellular extracts capable of carrying out protein synthesis upon addition of m-RNA. In such an assay, PNAs are added to the cellular extracts in addition to the m-RNAs to be translated. By comparing the translation products of the extracts containing PNAs to control assays without PNAs, inhibitory PNA sequences can be identified. Similarly, inhibition of m-RNA transcription can also be assessed using extracts that will synthesize specific m-RNA in response to added DNA from the gene of interest. The PNAs are added to the extracts and the m-RNA product therefrom is compared to the RNA product from extracts having only the DNA and no PNA added thereto. Alternatively, activation of gene transcription, rather than inhibition, can be assessed using the same system described above but measuring increased levels of m-RNA, instead of decreased levels, in the cell-free transcription system. Alternatively, activation of gene transcription can be assessed with transcription-active extracts. These extracts include genes coding for appropriate transcription repressors or attenuators. The DNA fragment of interest is added to the reaction. If addition of a particular PNA blocks inhibition of transcription, by for example, binding to the DNA encoding the transcription inhibitor, an increase in m-RNA production will result. Active sequences, identified by any of these methods, can then be analyzed, by the improved software system described below, to determine the optimum PNA sequence base identity and sequence length for affecting the target nucleotide sequence (generally, a DNA or RNA sequence).

Method for Optimizing Base Sequence and Sequence Length

According to the present invention a method for designing the most appropriate PNA oligomer(s) for affecting the target nucleotide sequence by optimizing the sequence base identity and sequence length of the PNA(s) is provided. The method uses an algorithm to manipulate data concerning the relationships between binding constants, structures and/or sequences of specific PNAs to predict optimal base sequence identities and sequence lengths of PNAs for use as potential therapeutic and/or diagnostic candidates. In addition, the software system contemplated herein can perform the rapid sequencing of newly discovered or poorly characterized genes. Additionally, where the sequence of a target gene is known, the algorithms contemplated herein can easily and quickly identify all possible complementary PNAs from the universal library, that should be tested for biological activity. This of course, greatly simplifies the screening process by dramatically reducing the number of individual PNA sequences that must be tested.

Preferably, when a double strand DNA with a known sequence is targeted, the sequences of both parallel and antiparallel strands are screened and tested, thereby doubling the effort in screening, while resulting in two sets of data for further analysis by the new algorithms provided herein. Ideally, of course, PNA candidates derived from the parallel strand should complement those derived from the antiparallel strand. However, to the degree such does not occur, for example, due to the inherent limitations of the testing methods, the software system contemplated herein will appropriately adapt its analysis to include relevant variable data while excluding spurious results. In operation, a set of data from the high throughput screening of the individual PNA oligomers is evaluated to determine an ideal sequence base identity and sequence length for binding to the target molecule and affecting that target's function as desired. First, an active hit is identified (for example, B4–B11 of the table below, wherein "B#" indicates the sequential location of the particular base). Next, additional PNA sequences from the library which overlap the sequence of the initial active hit, are identified and are ordered in single base shifts to the left or to the right of the initial hit. Data obtained from testing of the sequences identify the quality and quantity of activity for each sequence. As shown in the table below, the first overlapping sequence to the left of the B4–B11 sequence is B3–B10 and is active whereas the second overlapping sequence, B2–B9, is inactive, suggesting the left boundary for the optimal active PNA sequence is B3. Similarly, moving to the right, the sequence B5–B12 is active whereas the sequence B6–B13 is inactive, suggesting the right boundary for the optimal PNA sequence is B12. In this example then, the optimum PNA sequence is the decamer, B3–B12.

| A1 | A2 | A3 | A4 | A5 | A6 | A7 | A8 | A9 | A10 | A11 | A12 | A13 | A14 | Target |
|----|----|----|----|----|----|----|----|----|-----|-----|-----|-----|-----|--------|
|    |    |    | B4 | B5 | B6 | B7 | B8 | B9 | B10 | B11 |     |     |     | Initial Hit |
|    |    | B3 | B4 | B5 | B6 | B7 | B8 | B9 | B10 |     |     |     |     | Active |
|    | B2 | B3 | B4 | B5 | B6 | B7 | B8 | B9 |     |     |     |     |     | Inactive |
|    |    |    |    | B5 | B6 | B7 | B8 | B9 | B10 | B11 | B12 |     |     | Active |

-continued

| B6 | B7 | B8 | B9 | B10 | B11 | B12 | B13 | Inactive |
|----|----|----|----|----|----|----|----|----|

Further contemplated herein is use of the software system to trace a pattern of hybridization of labeled gene fragments to a PNA universal library in order to determine the sequence of the gene of interest. For example, a DNA fragment having an unknown sequence is labeled with a detectable probe and then hybridized with individual PNAs which are positioned on a support in a specific rule-based and traceable manner. Upon hybridization with a first PNA oligomer, software searches for related PNA sequences to determine to what degree the gene fragment binds thereto. This process continues until a full-length sequence for the fragment is determined. Performing this assay, simultaneously for numerous fragments from a single gene permits the rapid sequencing of those fragments and, therefore, of the gene.

While the invention herein disclosed has been described by means of specific embodiments and applications thereof, numerous modifications and variations could be made thereto by those skilled in the art without departing from the scope of the invention as set forth in the claims. By a protecting group is meant a labile moiety which forms a covalent bond with a primary or secondary amino and which can be removed (i.e. deprotected) by treatment with a reagent that does not harm a peptide (i.e. amide) bond. The use of such protecting groups in solid-phase and classical or liquid-phase synthesis is very well known, and although certain preferred amino protecting groups are disclosed, there are many other suitable groups that might be used instead. The disclosures of all U.S. patents mentioned hereinbefore are incorporated herein by reference.

Particular features of the invention are emphasized in the claims which follow.

What is claimed is:

1. A protected precursor which readily provides a peptide nucleic acid (PNA), said precursor consisting essentially of a cyclic substituted piperazinone having a nucleotide base covalently linked directly to one nitrogen in said cyclic piperazinone ring and having a first protecting group covalently linked to the other nitrogen in said piperazinone ring, said substituted piperazinone constituting an intermediate, which precursor may be readily hydrolyzed to a peptide nucleic acid monomer or reacted with a nucleophile to form a PNA derivative or an oligomer.

2. The precursor according to claim 1 wherein said nucleotide base is selected from the group consisting of thymine, cytosine, guanine, adenine, and universal bases which are capable of binding to any of the four natural nucleotide bases.

3. The precursor according to claim 1 wherein said linkage of said nucleotide base to said piperazinone includes an amide bond between an acetyl group substituted onto a nitrogen atom in a purine or a pyrimidine ring in said nucleotide base and said one nitrogen.

4. The precursor according to claim 3 wherein either an amino group linked to or an amido group that is a part of an aromatic ring of said nucleotide base has attached thereto at least one amino- or amido-protecting group as a second protecting group.

5. The precursor according to claim 4 wherein said second protecting group attached to said nucleotide base is one that is not normally removed under conditions which remove said first protecting group.

6. The precursor according to claim 5 wherein said first protecting group is Boc.

7. A method for preparing a protected precursor, which method comprises the steps of:
   a) mixing ethylene diamine and a haloacetic acid equivalent having the formula Y—CH$_2$CO—X where X is hydrogen, halogen or OR, with R being hydrogen or lower alkyl, and Y is a leaving group, in solution;
   b) heating said mixture of step (a) to form a cyclic piperazinone;
   c) covalently coupling a nucleotide base to said cyclic piperazinone to create a base-substituted piperazinone; and
   d) providing protection for an amido moiety of the product of step (c) to form an activated intermediate which serves as a precursor that may be readily hydrolyzed to a peptide nucleic (PNA) acid monomer or reacted with a nucleophile to form a PNA derivative or an oligomer.

8. The method according to claim 7 wherein said nucleotide base is selected from the group consisting of thymine, cytosine, guanine, adenine, and universal bases which are capable of binding to any of the four natural nucleotide bases.

9. The method according to claim 7 wherein said haloacetic acid equivalent is provided in at least a stoichiometric amount to said ethylene diamine and where X is H, Br, Cl or OR with R being H or lower alkyl.

10. The method according to claim 9 wherein said nucleotide base is added by initially treating said cyclic piperazinone with a haloacetylating agent to form an amide bond and create a haloacetyl-piperazinone which is subsequently reacted with said nucleotide base.

11. The method according to claim 10 wherein said leaving group is Cl or Br and said haloacetylating agent is chloroacetic anhydride or chloroacetylchloride.

12. The method according to claim 7 wherein said base-substituted piperazinone is further reacted to add a covalent amido-protecting group.

13. The method according to claim 12 wherein said further reaction is with di-t-butyl dicarbonate.

14. The method according to claim 7 wherein said nucleotide base is added to the secondary amino moiety in said piperazinone by reacting said cyclic piperazinone with a nucleotide base acetic acid to form said nucleotide base-piperazinone product.

15. The method according to claim 14 wherein said nucleotide base-piperazinone product is then reacted using a reagent selected from the group consisting of di-t-butyl dicarbonate, benzyl chloroformate and 2-nitrobenzenesulfonyl chloride, to protect the amido moiety in said piperazinone ring.

16. A method for preparing a protected precursor, which method comprises the steps of:
   a) carrying out a reductive amination reaction between the α-amino group of an α-amino acid or an ester thereof and the carboxyl group of either an N-protected amino aldehyde or an N-protected amino ketone;
   b) then deprotecting the primary amino group of the reaction product of a step (a);

c) heating said deprotected reaction product of step (b) to form a cyclic piperazinone;

d) covalently coupling a nucleotide base to said cyclic piperazinone to create a base-substituted piperazinone; and e) providing protection for an amido moiety of the product of step (d) to form an intermediate which serves as a precursor that may be readily hydrolyzed to a peptide nucleic acid (PNA) monomer or reacted with a nucleophile to form a PNA derivative or an oligomner.

17. The method according to claim 16 wherein said amino aldehyde has the formula $P^gHN—CHR_1—CHO$, said amino ketone has the formula $P^gHN—CHR_1—C(=O)—R_2$ and said α-amino acid or ester has the formula $H_2N—CHR_4—COOR_3$ wherein $P^g$ is an amino-protecting group, $R_1$, $R_3$ and $R_4$ are H, lower alkyl, substituted lower alkyl or aromatic, and $R_2$ is lower alkyl, substituted lower alkyl, or aromatic.

18. The method according to claim 16 wherein said nucleotide base is linked to the secondary amino group in said piperazinone ring through a linkage which includes an acetyl residue which is substituted onto a nitrogen atom in a purine or a pyrimidine ring in said nucleotide base and which forms an amide bond with said secondary amino group.

\* \* \* \* \*